United States Patent
Makino et al.

(10) Patent No.: US 11,672,770 B2
(45) Date of Patent: Jun. 13, 2023

(54) ORAL INGESTION COMPOSITION

(71) Applicant: THERAVALUES CORPORATION, Chiyoda-ku (JP)

(72) Inventors: Yuji Makino, Chiyoda-ku (JP); Tsukasa Takahashi, Chiyoda-ku (JP)

(73) Assignee: THERAVALUES CORPORATION, Chiyoda-ku (JP)

(*) Notice: Subject to any disclaimer, the term of this patent is extended or adjusted under 35 U.S.C. 154(b) by 323 days.

(21) Appl. No.: 16/970,748

(22) PCT Filed: Feb. 18, 2019

(86) PCT No.: PCT/JP2019/005898
§ 371 (c)(1),
(2) Date: Aug. 18, 2020

(87) PCT Pub. No.: WO2019/160146
PCT Pub. Date: Aug. 22, 2019

(65) Prior Publication Data
US 2021/0008007 A1      Jan. 14, 2021

(30) Foreign Application Priority Data
Feb. 19, 2018 (JP) .............................. JP2018-027317

(51) Int. Cl.
| A61K 31/12 | (2006.01) |
| A23K 10/30 | (2016.01) |
| A23L 33/105 | (2016.01) |
| A23L 2/52 | (2006.01) |
| A61K 9/00 | (2006.01) |
| A61K 47/38 | (2006.01) |

(52) U.S. Cl.
CPC .............. *A61K 31/12* (2013.01); *A23K 10/30* (2016.05); *A23L 2/52* (2013.01); *A23L 33/105* (2016.08); *A61K 9/0053* (2013.01); *A61K 47/38* (2013.01); *A23V 2002/00* (2013.01)

(58) Field of Classification Search
CPC ...................................................... A61K 31/12
See application file for complete search history.

(56) References Cited

U.S. PATENT DOCUMENTS

| 4,999,205 A | 3/1991 | Todd, Jr. | |
| 10,245,238 B2* | 4/2019 | Takeuchi | ................ A61P 1/16 |
| 2013/0274343 A1* | 10/2013 | Deshpande | .......... A61K 9/1694 |
| | | | 514/679 |
| 2013/0303628 A1 | 11/2013 | Breitenbach et al. | |
| 2017/0239194 A1* | 8/2017 | Takeuchi | ................ A61P 35/00 |
| 2017/0332664 A1 | 11/2017 | Vondran et al. | |
| 2017/0367997 A1 | 12/2017 | Kawakami et al. | |
| 2018/0289635 A1 | 10/2018 | Nakao et al. | |

FOREIGN PATENT DOCUMENTS

| JP | 3-97761 A | 4/1991 |
| JP | 11-92363 A | 4/1999 |
| JP | 2014-503470 A | 2/2014 |
| JP | 2017-538430 A | 12/2017 |
| WO | WO 2015/174475 A1 | 11/2015 |
| WO | WO 2016/010093 A1 | 1/2016 |
| WO | WO 2016/104657 A1 | 6/2016 |
| WO | WO 2017/061627 A1 | 4/2017 |

OTHER PUBLICATIONS

International Search Report dated May 7, 2019 in PCT/JP2019/005898 filed on Feb. 18, 2019, 2 pages.
Yoshioka, M. et al., "Crystallization of Indomethacin from the Amorphous State below and above its Glass Transition Temperature," Journal of Pharmaceutical Sciences, vol. 83, No. 12, Dec. 1994, pp. 1700-1705.
Kawakami, K. "Modification of physicochemical characteristics of active pharmaceutical ingredients and application of supersaturatable dosage forms for improving bioavailability of poorly absorbed drugs," Advanced Drug Delivery Reviews, vol. 64, 2012, pp. 480-495.
Kawakami, K. "Theory and practice of supersaturatable formulations for poorly soluble drugs," Therapeutic Delivery, vol. 6, No. 3, 2015, pp. 339-352.
Zhang, S. et al., "Coaxial Electrospray Formulations for Improving Oral Absorption of a Poorly Water-Soluble Drug," Molecular Pharmaceutics, vol. 8, 2011, pp. 807-813.

* cited by examiner

*Primary Examiner* — Rei Tsang Shiao

(74) *Attorney, Agent, or Firm* — Oblon, McClelland, Maier & Neustadt, L.L.P.

(57) ABSTRACT

A curcumin-containing composition has improved oral absorbability. An oral ingestion composition contains: (A) solid curcumin containing an amorphous body and/or an analog thereof; and (B) a solid water-soluble polymer which becomes viscous in an aqueous medium having a pH of 5 or more.

15 Claims, 13 Drawing Sheets

ORAL INGESTION COMPOSITION

FIELD OF THE INVENTION

The present invention relates to a curcumin-containing oral ingestion composition suitably used as a feed, a food and drink, or a pharmaceutical composition.

BACKGROUND OF THE INVENTION

In recent years, curcumin and an analog thereof have been attracting attention for their physiological activities such as an antioxidative action, an anti-inflammatory action, an antiallergic action, a tumorigenesis inhibitory action, a cholesterol lowering action, a brain disease preventive action, and a cardiovascular disease preventing and treating action. Applications thereof to, for example, a feed, a food and drink (for example, a functional food), a drug, and a cosmetic are under consideration. However, curcumin and an analog thereof have extremely low absorbability into the body upon oral ingestion. Therefore, the physiological activities of curcumin and an analog thereof cannot be sufficiently obtained by oral ingestion disadvantageously.

Therefore, as a means for improving the absorbability of curcumin and an analog thereof after oral ingestion, a means for forming a solid dispersion in which curcuminoid, a thermoplastic polymer, and phosphatide are melt-processed (Patent Literature 1), a means for forming a complex of curcumin and a polysaccharide (Patent Literature 2), and a means for forming a complex of curcumin and a water-soluble cellulose (Patent Literatures 3, 4, and 5) have been reported. There is also a report that a dissolution rate is improved by making curcumin amorphous (Non Patent Literatures 1 to 4).

CITATION LIST

Patent Literature

Patent Literature 1: JP 2014-503470 A
Patent Literature 2: JP H3-97761 A
Patent Literature 3: WO 2015/174475 A
Patent Literature 4: WO 2016/010093 A
Patent Literature 5: WO 2017/061627 A
Non Patent Literature
Non Patent Literature 1: J Pharm Sci. 1994 December; 83 (12): 1700-5.
Non Patent Literature 2: Adv Drug Deliv Rev. 2012 May 1; 64 (6): 480-95.
Non Patent Literature 3: Ther Deliv. 2015 March; 6 (3): 339-52.
Non Patent Literature 4: Mol Pharm. 2011 Jun. 6; 8 (3): 807-13.

SUMMARY OF THE INVENTION

Technical Problem

One of attempts to improve absorbability of a poorly absorbable material after oral ingestion is an amorphization technique. However, since a formulation using an amorphous body has lower chemical stability than a general crystalline formulation and causes recrystallization easily, it has been clarified that the formulation using an amorphous body has low physical stability (Non Patent Literatures 1 to 3). It has also been clarified that bioavailability of a solid dispersion partially containing a crystal is as low as a crystalline physical mixture relative to a completely amorphous solid dispersion (Non Patent Literature 4). From such a background, it has been difficult to formulate an amorphous body.

As a technique for stabilizing an amorphous body, there is formation of a solid dispersion with, for example, hydroxypropylmethylcellulose. For example, a technique has been reported in which a hydrophilic polymer such as hydroxypropylmethylcellulose, a nonionic surfactant such as a polyglycerin fatty acid ester, and crystalline curcumin are melt-kneaded to prepare an amorphous body of curcumin (Patent Literature 5). By the way, in a result of examining the absorbability after oral administration to a rat in Example 8 of the present invention under the same conditions as in Patent Literature 5, the absorbability is significantly higher than that in Example described in Patent Literature 5. In addition, the melt-kneading method has disadvantages such as degeneration of an excipient due to exposure of the excipient to a high temperature condition during melt-kneading, an increase in manufacturing cost due to complicated processing steps, and difficulty in establishing an industrial application technique.

Therefore, an object of the present invention is to provide a new curcumin-containing composition having favorable storage stability and improved absorbability after oral ingestion.

Solution to Problem

Therefore, the present inventor made various studies in order to develop a stable curcumin-containing composition having favorable absorbability after oral ingestion. As a result, surprisingly, the present inventor has found that a composition obtained by simply mixing solid curcumin containing an amorphous body and/or an analog thereof with a solid water-soluble polymer which becomes viscous in an aqueous medium having a pH of 5 or more significantly improves absorbability of curcumin and/or an analog thereof after oral ingestion, and has favorable storage stability, and has completed the present invention.

That is, the present invention provides the following [1] to [11].

[1] An oral ingestion composition containing: (A) solid curcumin containing an amorphous body and/or an analog thereof; and (B) a solid water-soluble polymer which becomes viscous in an aqueous medium having a pH of 5 or more.

[2] The oral ingestion composition according to [1], in which a content mass ratio (A/B) between components (A) and (B) is 0.1 to 570.

[3] The oral ingestion composition according to [1] or [2], in which the curcumin and/or an analog thereof is curcumin or a turmeric pigment.

[4] The oral ingestion composition according to any one of [1] to [3], in which (A) solid curcumin and/or an analog thereof contains (A-2) an amorphous body, or (A-2) the amorphous body and (A-1) a crystalline body.

[5] The oral ingestion composition according to [4], in which a content mass ratio (A-1/A-2) between components (A-1) and (A-2) is 0.67 or less.

[6] The oral ingestion composition according to any one of [1] to [5], in which component (B) is one or more water-soluble polymers selected from the group consisting of hydroxypropyl cellulose, hydroxypropyl methyl cellulose, carboxymethyl cellulose, carboxymethyl cellulose sodium, methyl cellulose, hydroxypropyl methyl cellulose acetate succinate, carboxymethyl ethyl cellulose, and hydroxypropyl methyl cellulose phthalate ester.

[7] The oral ingestion composition according to any one of [1] to [6], containing components (A) and (B) in a uniformly mixed state.

[8] The oral ingestion composition according to any one of [1] to [7], in which components (A) and (B) each have a particle size of 300 or less.

[9] A method for manufacturing a composition containing solid amorphous curcumin and/or an analog thereof and a solid water-soluble polymer which becomes viscous in an aqueous medium having a pH of 5 or more, the method including: an amorphization step of melting and then cooling curcumin and/or an analog thereof to prepare an amorphous body; and pulverizing and mixing individually or simultaneously the amorphous body prepared in the amorphization step and a solid water-soluble polymer which becomes viscous in an aqueous medium having a pH of 5 or more.

[10] The method for manufacturing a composition according to [9], in which the pulverizing and mixing step is performed by a pulverizing method selected from the group consisting of a rotary type pulverizing method, an air flow type pulverizing method, a high speed rotary type pulverizing method, a container driving type pulverizing method, and a medium stirring type pulverizing method.

[11] The oral ingestion composition according to any one of [1] to [8], selected from the group consisting of a feed, a food and drink, and a drug.

Advantageous Effects of the Invention

With the oral ingestion composition of the present invention, it was clarified that by simply mixing solid curcumin containing an amorphous body and/or an analog thereof with a solid water-soluble polymer which becomes viscous in an aqueous medium having a pH of 5 or more, absorbability of curcumin and/or an analog thereof after oral ingestion is significantly improved, and storage stability thereof is favorable. In addition, since the processing method of the present invention is simple mixing, an excipient is not exposed to a high temperature unlike a melt-kneading method, and characteristics of the excipient are sufficiently exhibited. Moreover, manufacturing cost is dramatically reduced by simplifying the processing steps.

DETAILED DESCRIPTION OF THE INVENTION

Figure 1:
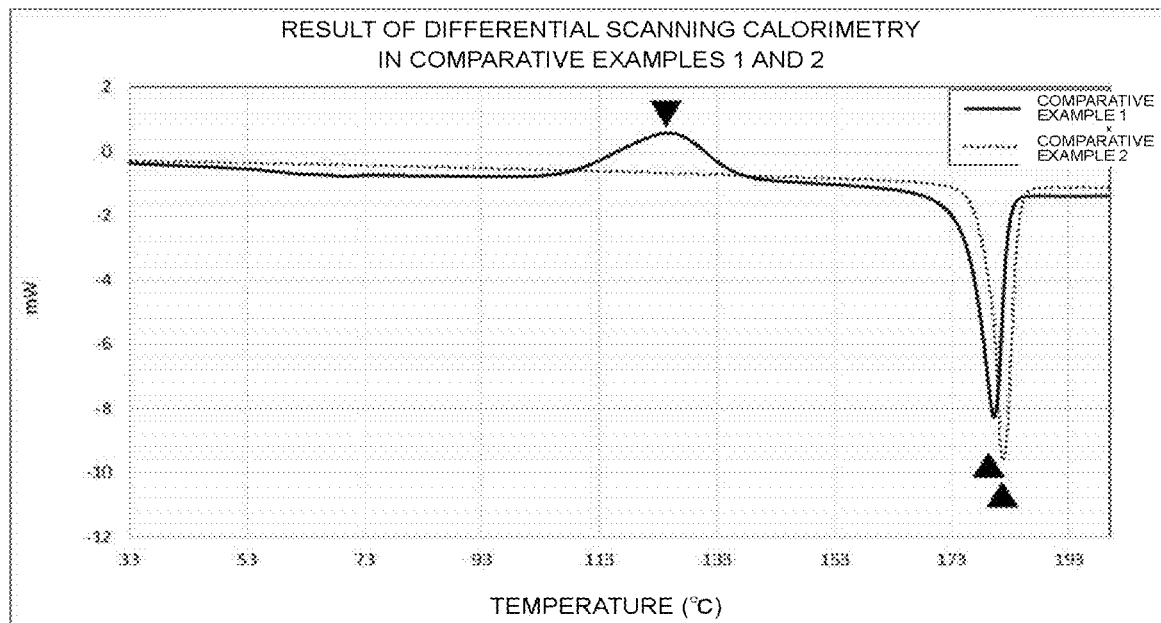
FIG. 1 illustrates results of calorimetry of curcumin-containing compositions (Comparative Examples 1 and 2).

An oral ingestion composition of the present invention contains (A) solid curcumin containing an amorphous body and/or an analog thereof and (B) a solid water-soluble polymer which becomes viscous in an aqueous medium having a pH of 5 or more.

Curcumin is a main component of curcuminoid contained in a turmeric pigment and is a compound represented by the following structural formula (1).

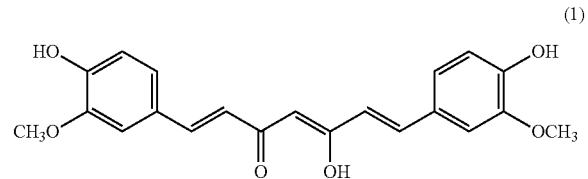

Curcumin used in the present invention may be chemically synthesized curcumin, or may be curcumin commercially available as a turmeric pigment. Examples of the turmeric pigment include: turmeric powder obtained by powdering a dried rhizome of a plant belonging to the turmeric genus of the ginger family (for example, Curcuma longa Linne); crude curcumin or oleoresin (turmeric oleoresin) obtained by extracting the turmeric powder using an appropriate solvent (for example, ethanol, oil and fat, propylene glycol, hexane, or acetone); and purified curcumin.

Note that curcumin includes both a keto-type and an enol-type which are tautomers.

Examples of the curcumin analog include demethoxycurcumin, bisdemethoxycurcumin, tetrahydrocurcumin, and hexahydrocurcumin. Note that the turmeric pigment contains curcumin, demethoxycurcumin, bisdemethoxycurcumin, and tetrahydrocurcumin.

Curcumin and/or an analog thereof used in the present invention contains an amorphous body. Amorphous curcumin can be confirmed by not having a clear diffraction peak in a powder X-ray diffraction spectrum. Amorphous curcumin can be obtained by melting curcumin at a temperature at which curcumin melts, for example 160° C. or higher.

The composition of the present invention contains (A-2) a solid amorphous curcumin. Here, the solid means a state of being in a form of powder, granules, or lumps, and indicates a state in which a complex is not formed with another substance or a solid dispersion is not formed. A fact that solid amorphous curcumin does not form a complex or a solid dispersion can be confirmed by a fact that solid amorphous curcumin has thermophysical properties similar only to those of amorphous curcumin in differential scanning calorimetry, and has thermophysical properties different from those of a complex or a solid dispersion. Of these solids, a powder-shaped solid of 300 μm or less is more preferable.

Component (A) of the composition of the present invention may contain, in addition to (A-2) amorphous curcumin and/or an analogue thereof (amorphous body), (A-1) crystalline curcumin and/or an analogue (crystalline body) thereof. The whole of component (A) may be formed of (A-2) the amorphous body. However, when component (A) contains both (A-1) and (A-2), a content mass ratio (A-1/A-2) between (A-1) a crystalline body and (A-2) an amorphous body is preferably 0.67 or less.

Component (B) of the composition of the present invention, a solid water-soluble polymer which becomes viscous in an aqueous medium having a pH of 5 or more, is preferably one or more selected from the group consisting of hydroxypropyl cellulose, hydroxypropyl methyl cellulose, carboxymethyl cellulose, carboxymethyl cellulose sodium, methyl cellulose, hydroxypropyl methyl cellulose acetate succinate, carboxymethyl ethyl cellulose, and hydroxypropyl methyl cellulose phthalate ester. These water-soluble polymers may have, for example, any molecular weight, any degree of substitution, or any branching property as long as they are used in a feed, a food and drink, a drug, or raw materials therefor.

The composition of the present invention contains (A) solid curcumin containing an amorphous body and/or an analog thereof, and (B) a solid water-soluble polymer which becomes viscous in an aqueous medium having a pH of 5 or more in a mixed state.

A content mass ratio (A/B) between components (A) and (B) in the composition of the present invention is preferably 0.1 to 570, more preferably 0.1 to 100, further preferably 0.5 to 50, and still further preferably 0.5 to 5.0 from a viewpoint of achieving both absorbability after oral ingestion and storage stability.

The composition of the present invention is easily manufactured by simply mixing components (A) and (B) in their original solid states. In order to make the whole of the composition solid, it is desirable to directly subjecting a mixture of components (A) and (B) to dry compression molding.

To the composition of the present invention, a feed, a food and drink, a drug, or components that can be used as raw materials therefor can be added unless it affects the amorphous state of curcumin. For example, magnesium stearate, calcium stearate or the like may be blended as a lubricant used during encapsulation, and corn starch or the like may be added as a space filler. In addition, it is preferable to use, for example, dextrin, crospovidone, carmellose, carmellose calcium, croscarmellose sodium, low-substituted hydroxypropyl cellulose, or crystalline cellulose, which acts as a disintegrant. Among these additives, it is preferable to add a disintegrant, and it is further preferable to use dextrin, crospovidone, carmellose, carmellose calcium, croscarmellose sodium, low-substituted hydroxypropyl cellulose, or crystalline cellulose. These disintegrants are preferably contained in an amount of 0.05 to 10 parts by mass with respect to 1 part by mass of component (A).

The composition of the present invention significantly improves absorbability of curcumin after oral ingestion and has favorable storage stability, as illustrated in Examples below. Therefore, the oral ingestion composition of the present invention is useful as a feed, an additive therefor, a dietary supplement, a functional food, a food for specified health use, a drug, a quasi-drug, a cosmetic, or raw materials therefor for exhibiting the physiological activities of curcumin and/or an analog thereof by oral ingestion.

The feed is not particularly limited as long as it contains the oral ingestion composition of the present invention, and can be used as, for example, a livestock feed for the purpose of fattening cattle, pigs, horses, and chickens, a feed for aquaculture of fish and crustaceans, an additive for antibacterial purposes, or a feed additive and a nutritional supplement for pets such as dogs and cats.

The food and drink is not particularly limited as long as it contains the oral ingestion composition of the present invention, and examples thereof include a food and drink containing curcumin. Specifically, it is considered that the food and drink can be provided as a food for specified health use, a food with a nutritional function, a food for elderly people, a food for a special purpose, a functional display food, or a health supplementary food (supplement), for example, with a display that the food and drink is used in order to adjust the function of the liver.

Examples of such a food and drink include: instant foods such as instant noodles, cup noodles, retort/cooked foods, cooked canned foods, microwave foods, instant soups/stews, instant miso soups/clear soups, canned soups, and freeze-dried foods; luxury drinks such as carbonated drinks, natural juices, juice drinks, soft drinks (including soft drinks containing juices), pulp drinks, fruit foods containing fruit grains, vegetable drinks, soy milk/soy milk drinks, coffee drinks, tea drinks, powdered drinks, concentrated drinks, sport drinks, nutrition drinks, and alcoholic drinks; flour foods such as bread, macaroni/spaghetti, noodles, cake mix, deep frying flour/bread crumbs, and skins of dumpling/spring roll; confectionery such as caramel/candy, chewing gum, chocolate, cookies/biscuits, cakes/pies, snacks/crackers, Japanese confectionery/rice confectionery/bean confectionery/baked confectionery, jelly, pudding, bavarois, and dessert confectionery; basic seasonings such as soy sauce, miso, sauces, processed tomato seasoning, mirin, vinegar, sweetener, fish sauce, and nyocumum; flavor seasonings; complex seasonings such as cooking mix, curry base, sauces, dressings, noodle soups, and spices; oil and fat foods such as butter, margarine, and mayonnaise; milk and dairy products such as milk/processed milk, milk drinks, yogurts, fermented milk drinks, lactic acid drinks, cheese, ice cream, modified milk powder, infant modified milk powder, and cream; egg processed foods such as liquid eggs, powdered eggs, and thinly shredded egg omelet; frozen foods such as semi-cooked frozen foods and cooked frozen foods; processed marine products such as canned seafood/paste, fish meat ham/sausage, seafood paste products, seafood delicacies, dried seafood products, and preserved food boiled in soy sauce; livestock processed products such as canned livestock/paste, livestock meat ham/sausage, and livestock delicacies; agricultural processed products such as canned agricultural products, canned fruits, fruit sauces, fruit preparations, jams/marmalades, pickles, boiled beans, dried agricultural products, and cereals; liquid foods; baby foods; weaning foods; seasoned powder to be sprinkled over rice; seaweed for hot tea-poured rice; nutritional foods such as bar foods; supplements; pills; hard capsules; and tablets [including uncoated tablets, sugar-coated tablets, rapidly disintegrating tablets, chewable tablets, effervescent tablets, troches, and film-coated tablets]. Note that these foods and drinks only need to be those obtained by adding the powder composition of the present invention to ready-made foods and drinks at the time of preparation, and an addition timing or an addition method is not particularly limited.

The pharmaceutical composition can be widely used as, for example, a drug or a quasi-drug. For example, a composition containing curcumin can be used for treating or preventing diseases such as dementia, diabetes, a cardiovascular disease, a digestive disease, a respiratory disease, a disease classified into otolaryngology, an autoimmune disease, a disease derived from skeletal muscles and joints, a disease classified into oral and dental fields, and malignant tumors.

A formulation form of the pharmaceutical composition is not particularly limited as long as it contains the powder composition of the present invention. Specific examples thereof include powders, granules, pills, capsules, tablets [including uncoated tablets, sugar-coated tablets, rapidly disintegrating tablets in the mouth, chewable tablets, effervescent tablets, troches, and film-coated tablets], dry syrups, film agents, and jelly agents, and also include confectionery agents (candies, gummy agents, and nougat agents]. Note that the capsules also include a soft capsule filled with a solution in which the powder composition of the present invention is dispersed in addition to a hard capsule.

The food and drink of the present invention and the pharmaceutical composition of the present invention can be prepared by appropriately blending, for example, a carrier, a base, and/or an additive which are usually used, for example, in the field of formulation or food within a range to achieve the purpose of the present invention in addition to the powder composition of the present invention.

EXAMPLES

Next, the present invention will be described in more detail with reference to Examples.

Example 1 to 5: Method for Manufacturing Physically Mixed Formulation

An appropriate amount of commercially available turmeric extract powder (curcumin content 86.8% (w/w)) was put into a hot plate type heating device (manufactured by Nisshin Kikai Co., Ltd.) and melted at a treatment temperature of 220° C. This melted product was held at room temperature to be solidified, and about 50 g of melted curcumin (amorphous curcumin) was thereby prepared.

Subsequently, the thus prepared melted curcumin was powdered in a mortar and caused to pass through a sieve having an opening of 250 µm (melted curcumin powder). The resulting powder was simply mixed with hydroxypropylmethylcellulose (HPMC) (Metolose SE-03 manufactured by Shin-Etsu Chemical Co., Ltd.) and maltodextrin (NSD #300 manufactured by San-ei Sucrochemical Co., Ltd.) as excipients for preparation (Example 1). Melted curcumin powder prepared in a similar manner to Example 1 was simply mixed with HPMC (Metolose SE-50 manufactured by Shin-Etsu Chemical Co., Ltd.) and maltodextrin (NSD #300 manufactured by San-ei Sucrochemical Co., Ltd.) for preparation (Examples 2, 3, 4, and 5).

Examples 6 and 7: Method for Manufacturing Physically Mixed Formulation for each Excipient Melted curcumin powder prepared in a similar manner to Example 1 was simply mixed with HPMC (Metolose SE-50 manufactured by Shin-Etsu Chemical Co., Ltd.) or hydroxypropyl methylcellulose acetate succinate (HPMCAS) (AQOAT™AS-MF manufactured by Shin-Etsu Chemical Co., Ltd.) for preparation (Examples 6 and 7).

Example 8: Method for Manufacturing Physically Mixed Formulation on Industrial Application Scale Melted curcumin prepared in a similar manner to Example 1 was roughly crushed using a cutter mill VM (manufactured by Makino Sangyo Co., Ltd.) with an installation screen width of 5 mm. Thereafter, the resulting product was mixed with HPMC (Metolose SE-50 manufactured by Shin-Etsu Chemical Co., Ltd.) and maltodextrin (NSD #300 manufactured by San-ei Sucrochemical Co., Ltd.). The resulting mixture was simultaneously pulverized and mixed under a condition of a treatment rate of 60 kg/h per unit time using a single track jet mill STJ-200 for preparation (Example 8).

Examples 9 to 12: Method for Manufacturing Crystalline Curcumin-Containing Physically Mixed Formulation Into melted curcumin powder prepared in a similar manner to Example 1, crystalline curcumin was mixed in a fixed ratio. The resulting mixture was simply mixed with HPMC (Metolose SE-50 manufactured by Shin-Etsu Chemical Co., Ltd.) and maltodextrin (NSD #300 manufactured by San-ei Sucrochemical Co., Ltd.) for preparation (Examples 9, 10, 11, and 12).

Comparative Examples 1 to 8: Method for Manufacturing Curcumin-Containing Formulation Melted curcumin powder prepared in a similar manner to Example 1 (Comparative Example 1), commercially available turmeric extract powder (Comparative Example 2), a simple mixture of commercially available turmeric extract powder, HPMC (Metolose SE-50 manufactured by Shin-Etsu Chemical Co., Ltd.), and maltodextrin (NSD #300 manufactured by San-ei Sucrochemical Co., Ltd.) (Comparative Example 3), a simple mixture obtained by adding 0.00175 parts by mass of trace HPMC (Metolose SE-50 manufactured by Shin-Etsu Chemical Co., Ltd.) and maltodextrin (NSD #300 manufactured by San-ei Sucrochemical Co., Ltd.) to 1 part by mass of melted curcumin powder prepared in a similar manner to Example 1 (Comparative Example 4), and a simple mixture of melted curcumin powder prepared in a similar manner to Example 1, Sodium Starch Octenylsuccinate (AMYCOL NYUKA D manufactured by Nippon Starch Chemical Co., Ltd.), xylitol (manufactured by B Food Science Co., Ltd.), maltodextrin (NSD #300 manufactured by San-ei Sucrochemical Co., Ltd.), and microcrystalline cellulose (FD-101 manufactured by Asahi Kasei Chemicals Co., Ltd.) (Comparative Examples 5, 6, 7, and 8) were prepared.

Comparative Examples 9 to 14: Method for Manufacturing Composition Containing Amorphous Body of other Compound (1) Preparation of Amorphous Nifedipine Nifedipine was dissolved in ethyl alcohol, deionized water was gradually added thereto, and precipitated nifedipine was separated and dried to obtain powder. The precipitate was confirmed to be amorphous nifedipine by powder X-ray diffraction.

(2) Preparation of Mixed Composition

Amorphous nifedipine prepared in (1) was powdered in a mortar and caused to pass through a sieve having an opening of 250 μm. The resulting powder, a water-soluble polymer that had passed through a sieve having an opening of 250 μm (sodium starch octenylsuccinate(AMYCOL NYUKA D manufactured by Nippon Starch Chemical Co.)), HPMCAS (AQOAT™AS-MF manufactured by Shin-Etsu Chemical Co., Ltd.), xylitol (manufactured by B Food Science Co., Ltd.), maltodextrin (NSD #300 manufactured by San-ei Sucrochemical Co., Ltd.), microcrystalline cellulose (FD-101 manufactured by Asahi Kasei Chemicals Co., Ltd.), and HPMC (Metolose SE-50 manufactured by Shin-Etsu Chemical Co., Ltd.) were simply mixed for preparation (Comparative Examples 9, 10, 11, 12, 13, and 14).

Reference Examples 1 and 2-1 to 2-3: Method for Manufacturing Complex (Solid Dispersion)

Melted curcumin powder prepared in a similar manner to Example 1, HPMC (Metolose SE-03 manufactured by Shin-Etsu Chemical Co., Ltd.), maltodextrin (NSD #300 manufactured by San-ei Sucrochemical Co., Ltd.), and 180 g of ³⁄₁₆ inch iron balls (SUJ2) (a filling ratio with respect to the volume (50 mL) of a mixing and crushing container was set to about 80%) were put into the mixing and crushing container (50 mL PE tube). The mixing and crushing container was attached to a vortex mixer (MyLab #SLV-6 type manufactured by SLB), and mixing and crushing were performed to prepare a powdery amorphous curcumin-containing complex (solid dispersion) (Reference Example 1). Mixing and crushing conditions were an amplitude of ±5.0 mm and a frequency of 3000 rpm. The HPMC Metolose SE-03 used in Reference Example 1 was replaced with SE-50, and complexing was performed for 30 minutes (Reference Example 2-1), for 60 minutes (Reference Example 2-2), and for 120 minutes (Reference Example 2-3) in a similar manner to Example 1 to prepare formulations.

Table 1 illustrates the composition, the type of water-soluble polymer or the like, presence/absence of melting of curcumin, and complexing time in each of Examples 1 to 12, Comparative Examples 1 to 8, and Reference Examples 1 and 2-1 to 2-3. Table 2 illustrates the composition, the type of water-soluble polymer or the like, presence/absence of melting of nifedipine, and complexing time in each of Comparative Examples 9 to 14.

TABLE 1

| | Curcumin:Water-soluble polymer or the like:Dextrin | Type of water-soluble polymer or the like | Curcumin used was melted or not melted | Complexing time |
|---|---|---|---|---|
| Example 1 | 1:2:0.63 | HPMC(SE-03) | Melted | 0 minutes |
| Example 2 | 1:2:0.63 | HPMC(SE-50) | Melted | 0 minutes |
| Example 3 | 1:1:0.42 | HPMC(SE-50) | Melted | 0 minutes |
| Example 4 | 1:0.5:0.32 | HPMC(SE-50) | Melted | 0 minutes |
| Example 5 | 1:0.2:0.25 | HPMC(SE-50) | Melted | 0 minutes |
| Example 6 | 1:2:0 | HPMC(SE-50) | Melted | 0 minutes |
| Example 7 | 1:2:0 | HPMCAS | Melted | 0 minutes |
| Example 8 | 1:1:0.42 | HPMC(SE-50) | Melted | 0 minutes |
| Example 9 | 1:1:0.42 | HPMC(SE-50) | Not melted10%(w/w) Melted90%(w/w) | 0 minutes |
| Example 10 | 1:1:0.42 | HPMC(SE-50) | Not melted20%(w/w) Melted80%(w/w) | 0 minutes |
| Example 11 | 1:1:0.42 | HPMC(SE-50) | Not melted30%(w/w) Melted70%(w/w) | 0 minutes |
| Example 12 | 1:1:0.42 | HPMC(SE-50) | Not melted40%(w/w) Melted60%(w/w) | 0 minutes |
| Comparative Example 1 | 1:0:0 | — | Melted | 0 minutes |
| Comparative Example 2 | 1:0:0 | — | Not melted | 0 minutes |
| Comparative Example 3 | 1:2:0.63 | HPMC(SE-50) | Not melted | 0 minutes |
| Comparative Example 4 | 1:0.00175:0.21 | HPMC(SE-50) | Melted | 0 minutes |
| Comparative Example 5 | 1:2:0 | Modified-starch | Melted | 0 minutes |

TABLE 1-continued

|  | Curcumin:Water-soluble polymer or the like:Dextrin | Type of water-soluble polymer or the like | Curcumin used was melted or not melted | Complexing time |
|---|---|---|---|---|
| Comparative Example 6 | 1:2:0 | Xylitol | Melted | 0 minutes |
| Comparative Example 7 | 1:2:0 | Maltodextrin | Melted | 0 minutes |
| Comparative Example 8 | 1:2:0 | Microcrystalline Cellulose | Melted | 0 minutes |
| Reference Example 1 | 1:2:0.63 | HPMC(SE-03) | Melted | 30 minutes |
| Reference Example 2-1 | 1:2:0.63 | HPMC(SE-50) | Melted | 30 minutes |
| Reference Example 2-2 | 1:2:0.63 | HPMC(SE-50) | Melted | 60 minutes |
| Reference Example 2-3 | 1:2:0.63 | HPMC(SE-50) | Melted | 120 minutes |

TABLE 2

|  | Nifedipine:Water-soluble polymer or the like:Dextrin | Type of water-soluble polymer or the like | Nifedipine used was melted or not melted | Complexing time |
|---|---|---|---|---|
| Comparative Example 9 | 1:2:0 | Sodium Starch Octenylsuccinate | Melted | 0 minutes |
| Comparative Example 10 | 1:2:0 | HPMCAS | Melted | 0 minutes |
| Comparative Example 11 | 1:2:0 | Xylitol | Melted | 0 minutes |
| Comparative Example 12 | 1:2:0 | Maltodextrin | Melted | 0 minutes |
| Comparative Example 13 | 1:2:0 | Microcrystalline Cellulose | Melted | 0 minutes |
| Comparative Example 14 | 1:2:0 | HPMC (SE-50) | Melted | 0 minutes |

Example 13: Differential Scanning Calorimetry of Physically Mixed Formulation

In order to examine that the thermophysical properties of the physically mixed formulation (Example 1) prepared by the method of the present invention are similar to those of amorphous curcumin (Comparative Example 1), and that the thermophysical properties of the physically mixed formulation (Example 1) prepared by the method of the present invention are different from those of the commercially available turmeric extract powder (Comparative Example 2) and the complex (solid dispersion, Reference Example 1), analysis was performed using a differential scanning calorimeter DSC-60 (manufactured by Shimadzu Corporation) under temperature raising conditions: 10° C/min within measurement range: room temperature to 200° C. Note that measurement was also performed for Comparative Examples 1 and 2 and Reference Example 1 under the same conditions.

As illustrated in FIG. 1, the melted curcumin powder in Comparative Example 1 exhibited heat generation due to a change from an amorphous body to a crystalline body while the temperature changed from 113 to 133° C. An endothermic reaction due to melting of crystalline curcumin was observed while the temperature changed from 173 to 193° C. both in Comparative Examples 1 and 2.

Figure 2:
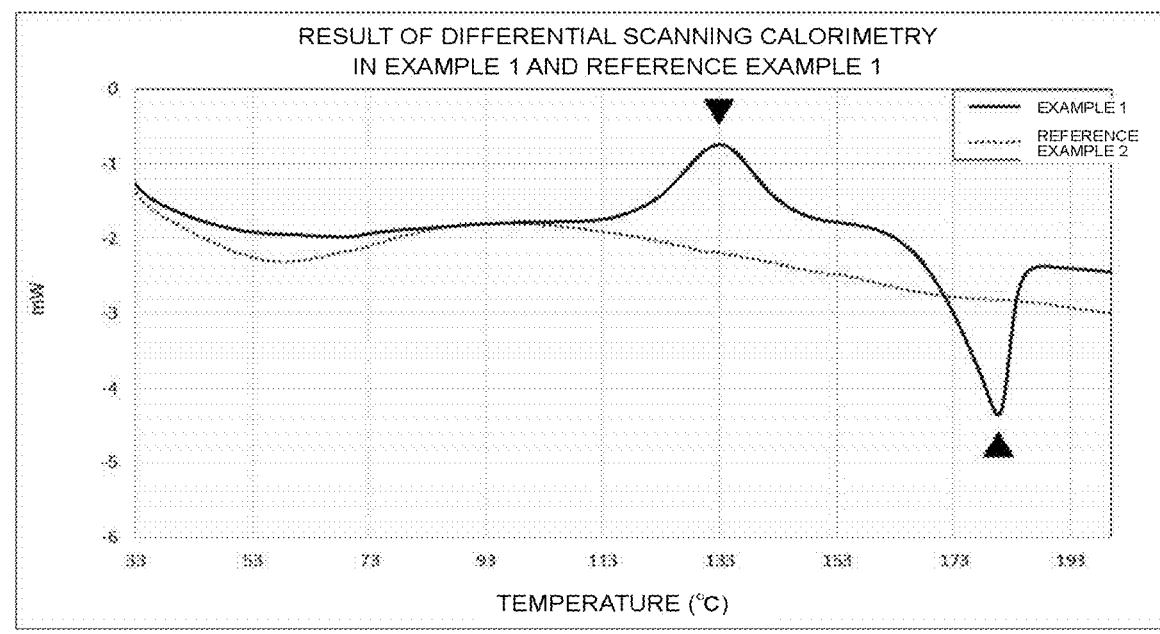
FIG. 2 illustrates results of calorimetry of curcumin-containing compositions (Example 1 and Reference Example 1).

As illustrated in FIG. 2, in Reference Example 1 of the complex (solid dispersion), no heat generation due to recrystallization of curcumin and no endotherm near the melting point of crystalline curcumin were observed. Meanwhile, regarding the thermophysical properties of the physically mixed formulation prepared by the method of the present invention (Example 1), heat generation due to recrystallization of curcumin around 133° C. and endotherm due to melting of crystalline curcumin while the temperature changed from 173 to 193° C. were observed, similarly to Comparative Example 1. The thermophysical properties of the physically mixed formulation prepared by the method of the present invention (Example 1) were found to be completely different from those of the crystalline curcumin (Comparative Example 2) and the complex (solid dispersion) (Reference Example 1).

Example 14: Bright Field Observation Image in Example 2

The physically mixed formulation (Example 2) prepared by the method of the present invention was observed using a CCD fluorescence microscope BZ-X800 (manufactured by KEYENCE CORPORATION).

Figure 3:
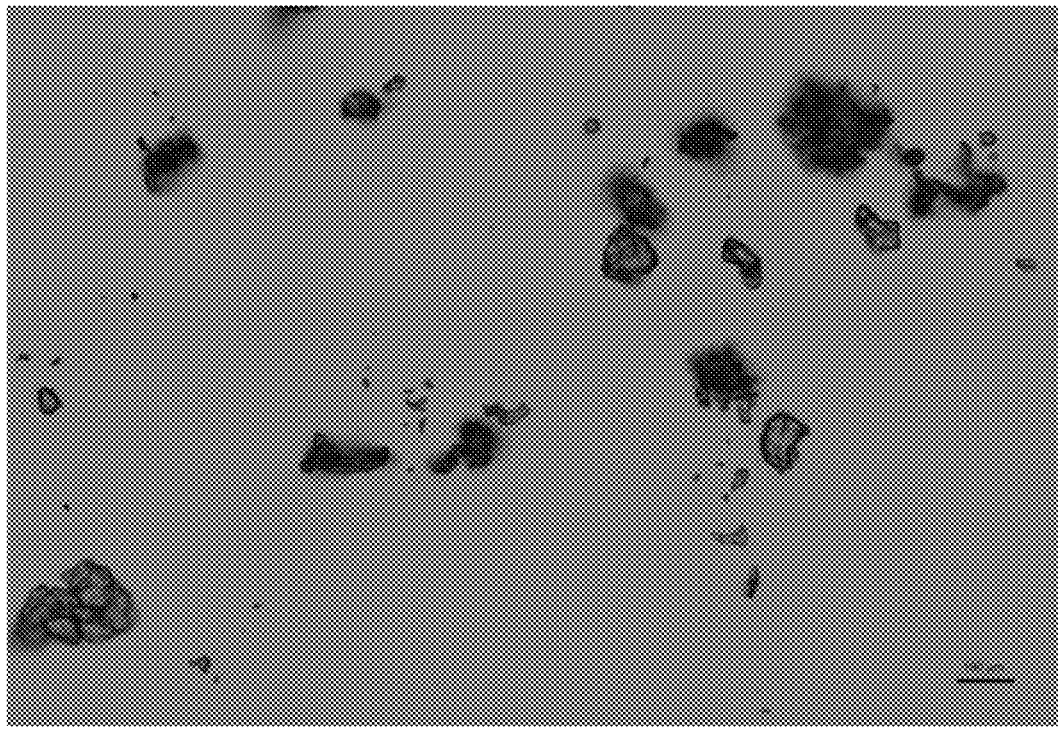
FIG. 3 illustrates a bright field observation image of a curcumin-containing composition (Example 2).

As illustrated in FIG. 3, the physically mixed formulation of the present invention was found to have a particle size of 300 μm or less.

Example 15: Absorbability Test after Oral Administration to Rat in Example 2

(1) Administration Method

To a 8 to 9 week-old male SD rat, a suspension obtained by suspending the amorphous curcumin-containing physically mixed formulation in Example 2 in physiological saline was forcibly orally administered such that the curcumin concentration was 10 mg/kg. Blood was collected before administration, 30 minutes after administration, one hour after administration, and two hours after administration, and the total curcumin concentration in plasma collected by the method described below was measured. Note that as a control, the melted curcumin powder in Comparative Example 1, the commercially available turmeric extract powder in Comparative Example 2, the simple mixture of commercially available turmeric extract powder, HPMC (Metolose SE-50 manufactured by Shin-Etsu Chemical Co., Ltd.), and maltodextrin (NSD #300 manufactured by San-ei Sucrochemical Co., Ltd.) in Comparative Example 3, and a superabsorbent curcumin formulation (Theracurmin™: CR-033P) available from Theravalues as a ready-made product were used.

(2) Measurement of Curcumin Concentration in Plasma a. Pretreatment

To 20 μL of plasma, 100 μL of 0.1 M acetate buffer (pH 5.0) and 10 μL of β-glucuronidase solution (about 68,000 units/mL) were added, and the resulting mixture was held at 37° C. for one hour. Thereafter, 10 μL of 50% (v/v) methanol containing 20 ng/mL of mepronil, which is an internal standard solution, and 0.5 mL of chloroform were added thereto. The resulting mixture was stirred for one minute using a vortex mixer, and then mixed for 15 minutes using an ultrasonic generator. Next, the resulting solution was separated into a chloroform layer and an aqueous layer by centrifugation (13,000×g, five minutes, room temperature). This extraction operation was repeated twice. Thereafter, the chloroform layer was collected, and the solvent was distilled off from the chloroform layer using a vacuum centrifugal concentrator to obtain a dried solid product. To the product, 100 μL of 506 (v/v) methanol was added. The resulting mixture was centrifuged (13,000×g, five minutes, room temperature), and the supernatant was collected.

b. Measuring Method

By analyzing 2 μL of the supernatant prepared in the above column a. using LC-MS/MS (manufactured by Shimadzu Corporation), a curcumin concentration in plasma was measured. Note that regarding LC-MS/MS analysis conditions, Atlantis T3 (2.1×150 mm, 3 μm, manufactured by Waters) was used for an LC column, a column temperature was set to 40° C., a flow rate was set to 0.2 mL/min, and a mobile phase of A: 0.1% (v/v) formic acid aqueous solution and B: 0.1% (v/v) formic acid/acetonitrile was used. Gradient elution was performed under the conditions illustrated in Table 3. Regarding the MS analysis conditions, Electron Spray thermo ionization (ESI), Positive was used for an ionization mode, and Multiple Reaction Monitoring (MRM) was used for a measurement mode. Evaluation was performed from 369.1 to 177.2 (m/z) for curcumin and from 270 to 119 (m/z) for mepronil.

Meanwhile, a calibration curve used for quantifying the amount of curcumin contained in a sample was created by performing measurement under similar conditions to the above using a standard solution (curcumin concentration 0.9 to 225 ng/mL) prepared by adding 10 μL of 50% (v/v) methanol solution containing 20 ng/mL mepronil to 90 μL of a 50% (v/v) methanol solution containing 1.0, 2.0, 3.9, 7.8, 15.6, 31.3, 62.5, 125, or 250 ng/mL curcumin (curcumin standard solution).

TABLE 3

| | Gradient elution conditions | | | | |
|---|---|---|---|---|---|
| | Time(min) | | | | |
| | 0 | 1.8 | 7 | 7.01 | 15 |
| A(%) | 40 | 5 | 5 | 40 | 40 |
| B(%) | 60 | 95 | 95 | 60 | 60 |

(3) Result

Figure 4:
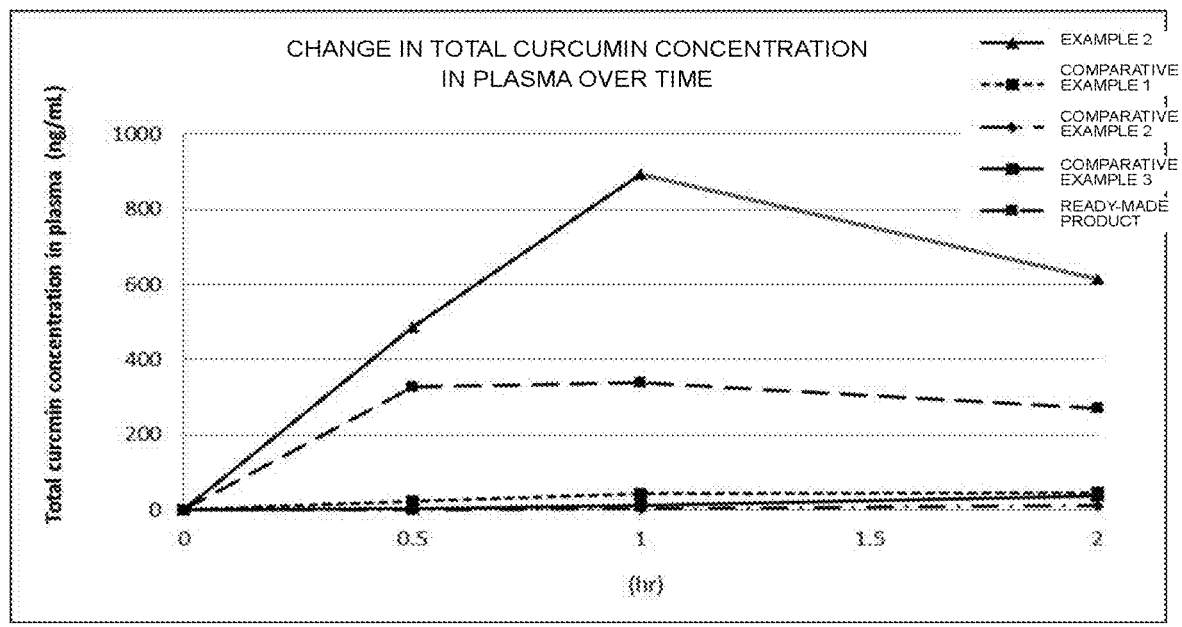
FIG. 4 illustrates absorbability (change over time) of curcumin-containing compositions (Example 2, Comparative Examples 1 to 3, and a ready-made product) after oral administration.
Figure 5:
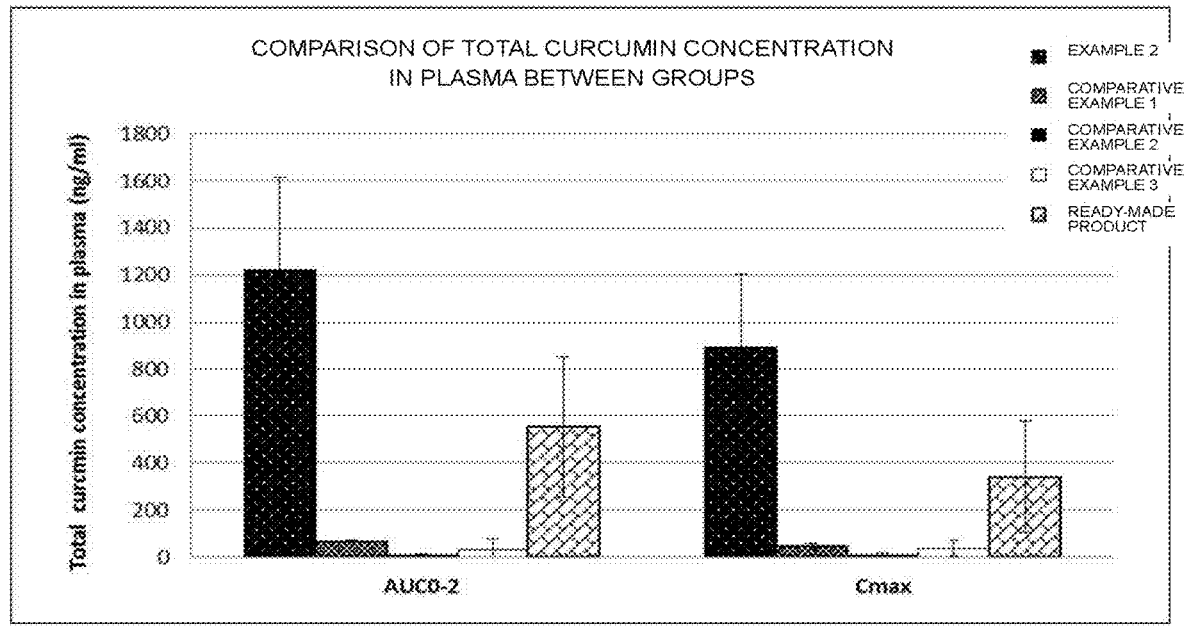
FIG. 5 illustrates absorbability (AUC and Cmax) of curcumin-containing compositions (Example 2, Comparative Examples 1 to 3, and a ready-made product) after oral administration.

A change in total curcumin concentration in plasma over time, a maximum blood concentration of total curcumin in plasma (Cmax (ng/mL)), and the area under total curcumin concentration in plasma-time curve (AUC (ng/mL·0-2 h)) are illustrated in FIGS. 4 and 5 and Table 4.

As illustrated in Table 4, the values of Cmax and AUC increased in order of Comparative Example 2, Comparative Example 3, Comparative Example 1, the ready-made product, and Example 2 prepared by the method of the present invention. Example 2 prepared by the method of the present invention had significantly higher absorbability than Comparative Examples and the ready-made product.

TABLE 4

| Administration sample | Cmax (ng/mL) | AUC (ng/mL · 0-2 h) |
|---|---|---|
| Example 2 | 892.4 ± 309.0 | 1218.8 ± 394.1 |
| Comparative Example 1 | 46.5 ± 35.2 | 66.8 ± 49.3 |
| Comparative Example 2 | 10.9 ± 9.3 | 8.2 ± 7.3 |
| Comparative Example 3 | 37.4 ± 13.7 | 29.8 ± 5.2 |
| Ready-made product | 339.8 ± 236.7 | 553.8 ± 298.6 |

Example 16: Absorbability Test after Oral Administration to Rat in Examples 3 to 5

(1) Administration Method

To a 8 week-old male SD rat, a suspension obtained by suspending each of the amorphous curcumin-containing physically mixed formulations in Example 3 to 5 in physiological saline was forcibly orally administered such that the curcumin concentration was 10 mg/kg. Blood was collected before administration, 30 minutes after administration, one hour after administration, and two hours after administration. Note that as a control, Comparative Example 4 and a superabsorbent curcumin formulation (Theracurmin™: CR-033P) available from Theravalues as a ready-made product were used. The total curcumin concentration in plasma collected was measured by the method described in Example 15.

(2) Result

Figure 6:
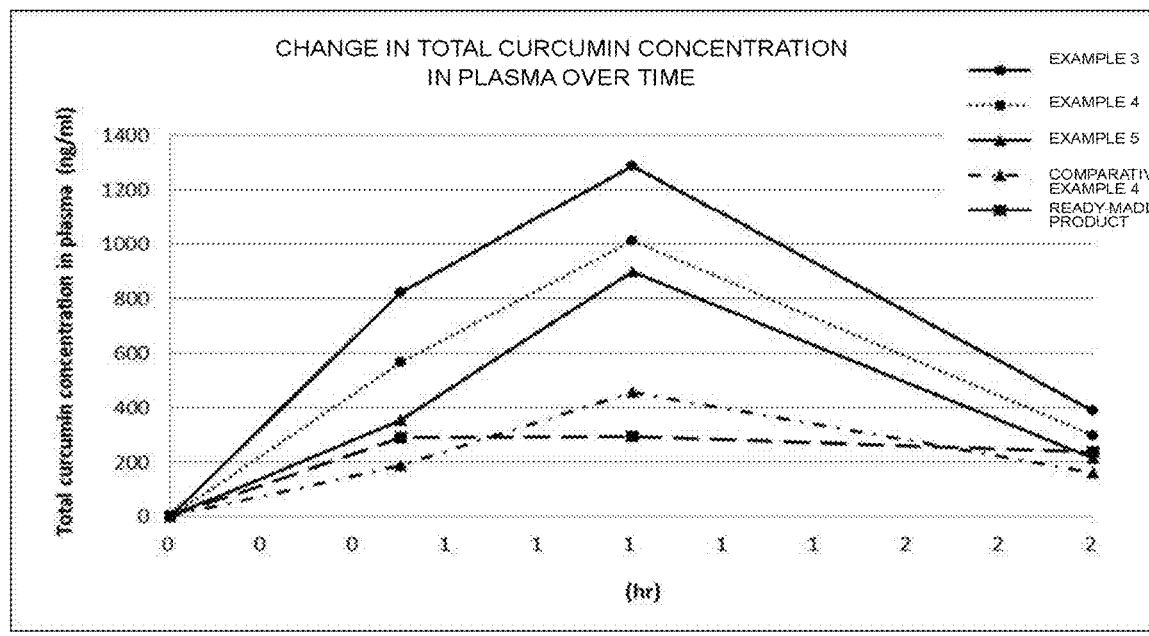
FIG. 6 illustrates absorbability (change over time) of curcumin-containing compositions (Examples 3 to 5, Comparative Example 4, and a ready-made product) after oral administration.
Figure 7:
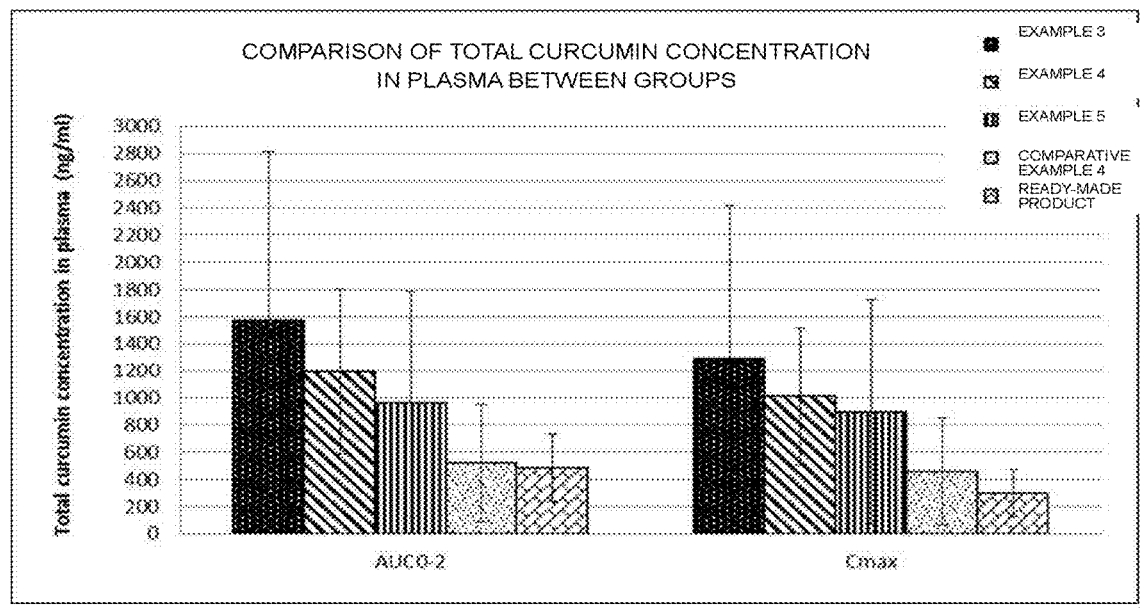
FIG. 7 illustrates absorbability (AUC and Cmax) of curcumin-containing compositions (Examples 3 to 5, Comparative Example 4, and a ready-made product) after oral administration.
Figure 8:
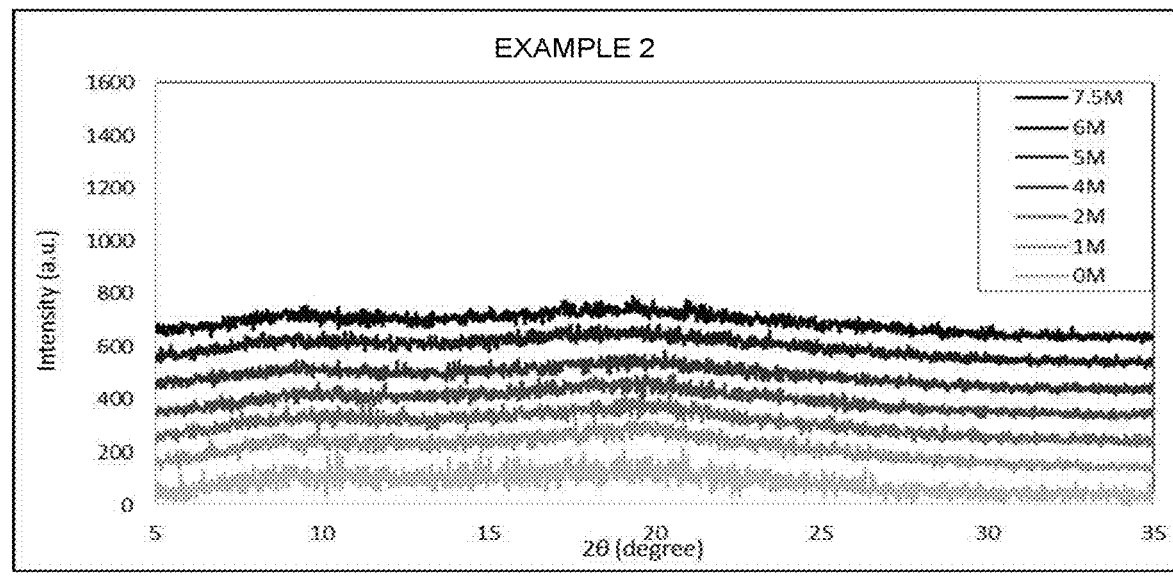
FIG. 8 illustrates storage stability (P-XRD) of a curcumin-containing composition (Example 2).
Figure 9:
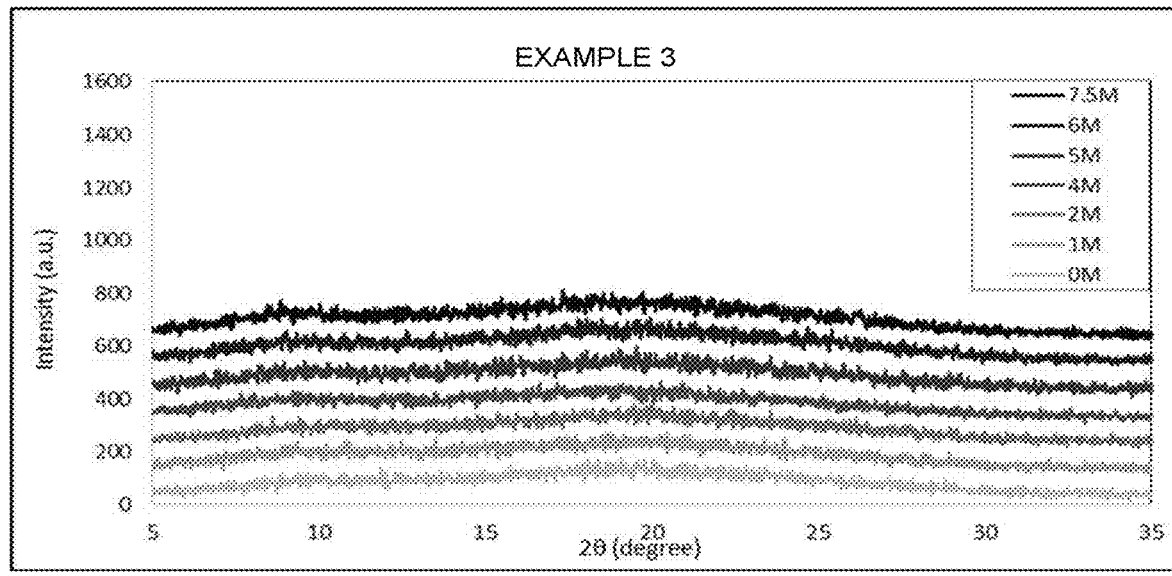
FIG. 9 illustrates storage stability (P-XRD) of a curcumin-containing composition (Example 3).
Figure 10:
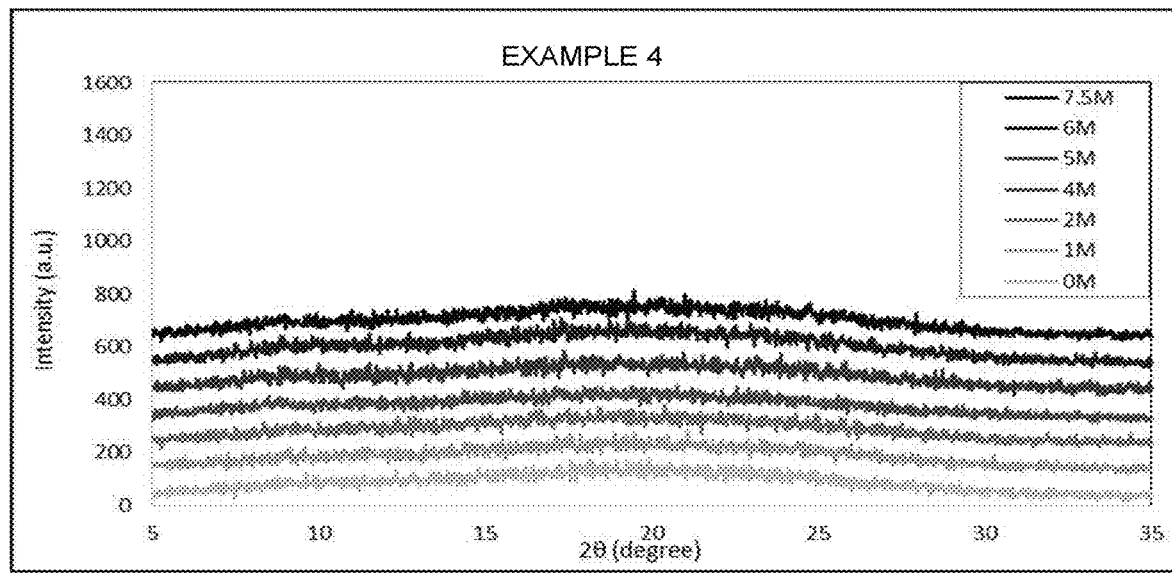
FIG. 10 illustrates storage stability (P-XRD) of a curcumin-containing composition (Example 4).
Figure 11:
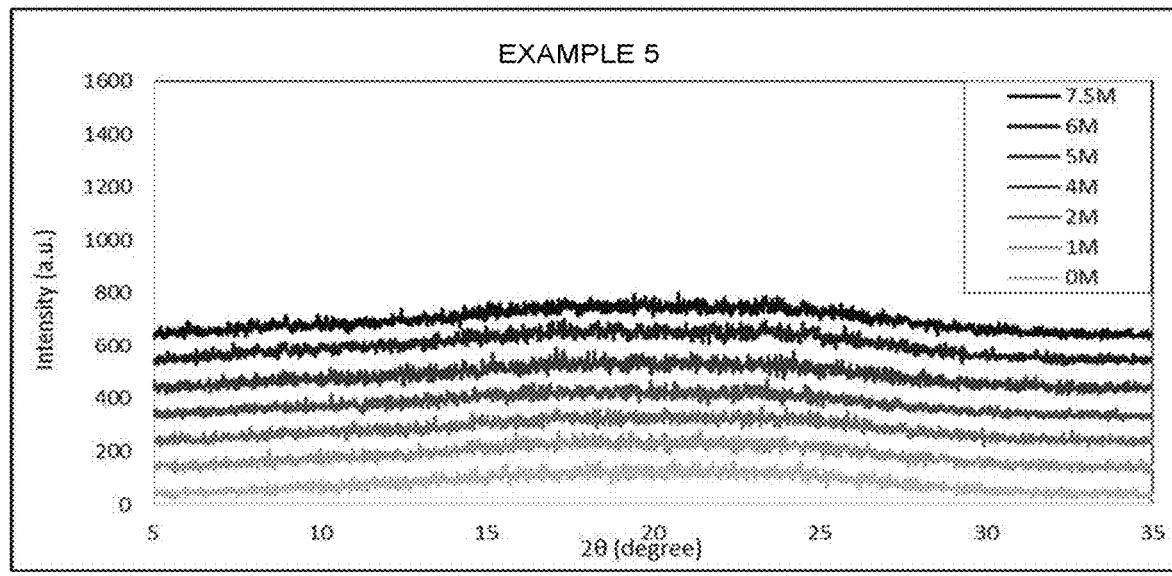
FIG. 11 illustrates storage stability (P-XRD) of a curcumin-containing composition (Example 5).

A change in total curcumin concentration in plasma over time, a maximum blood concentration of total curcumin in plasma (Cmax (ng/mL)), and the area under total curcumin concentration in plasma-time curve (AUC (ng/mL·0-2 h)) are illustrated in FIGS. 6 and 7 and Table 5.

As illustrated in Table 5, the values of Cmax and AUC increased in order of the ready-made product, Comparative Example 4, Example 5, Example 4, and Example 3.

TABLE 5

| Administration sample | Cmax (ng/mL) | AUC (ng/mL · 0-2 h) |
|---|---|---|
| Example 3 | 1287.7 ± 1133.0 | 1573.7 ± 1236.9 |
| Example 4 | 1011.1 ± 506.5 | 1192.2 ± 607.3 |
| Example 5 | 899.0 ± 827.1 | 959.3 ± 825.3 |
| Comparative Example 4 | 458.1 ± 393.6 | 520.5 ± 432.5 |
| Ready-made product | 297.1 ± 174.6 | 487.0 ± 250.8 |

Example 17: Acceleration Test Results of Examples 2 to 5, Comparative Examples 1 and 4, and Reference Examples 2-1 to 2-3

In order to examine stability of amorphous curcumin in each of the physically mixed formulations prepared by the method of the present invention (Examples 2 to 5), the melted curcumin powder (Comparative Example 1), the simple mixture obtained by adding 0.00175 parts by mass of trace HPMC to 1 part by mass of melted curcumin powder (Comparative Example 4), and the complex (solid dispersion: Reference Examples 2-1 to 2-3), each of Examples 2 to 5, Comparative Examples 1 and 4, and Reference Examples 2-1 to 2-3 was put in an aluminum pouch and held at 40° C. Crystallinity of curcumin was examined using a powder X-ray diffractometer (RINT-Ultima III manufactured by Rigaku) at the start of the test (0 M) and 1 to 7.5 months after the start of the test (1 to 7.5 M).

Figure 12:
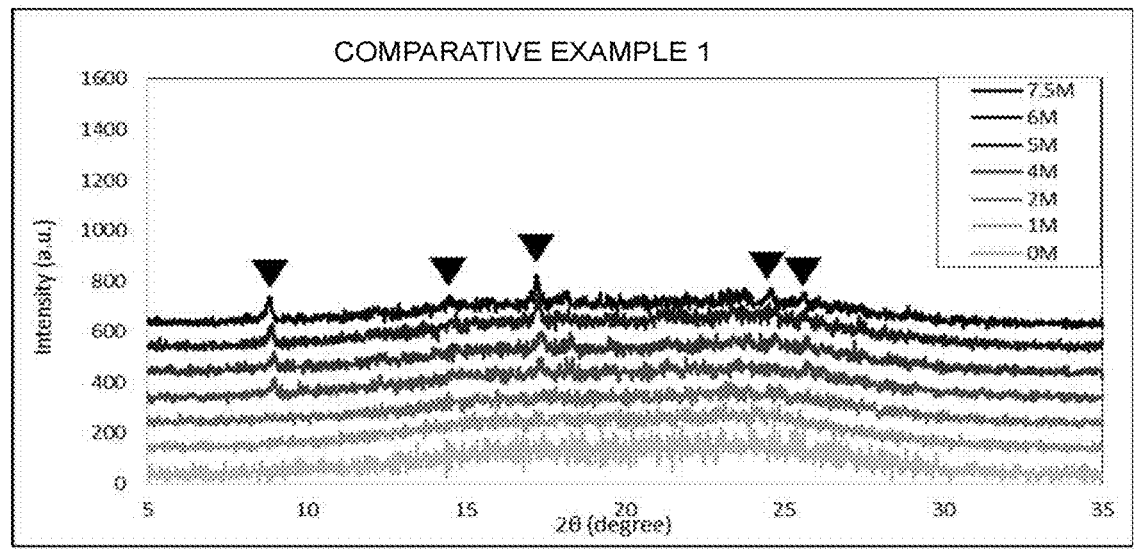
FIG. 12 illustrates storage stability (P-XRD) of amorphous curcumin (Comparative Example 1).
Figure 13:
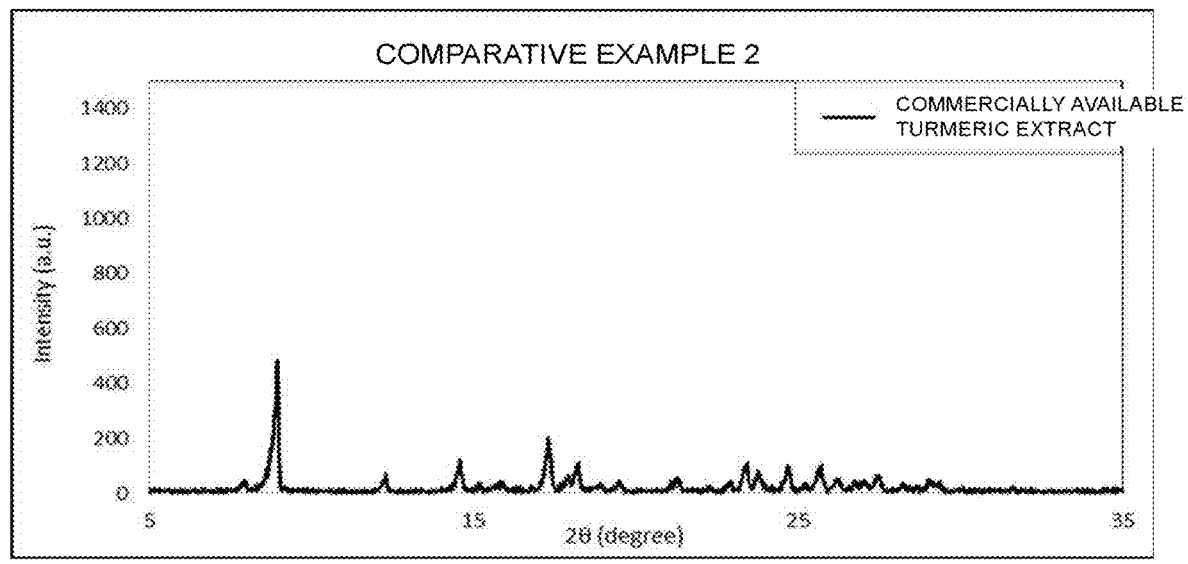
FIG. 13 illustrates a powder X-ray diffraction measurement result (P-XRD) of crystalline curcumin (Comparative Example 2).
Figure 14:
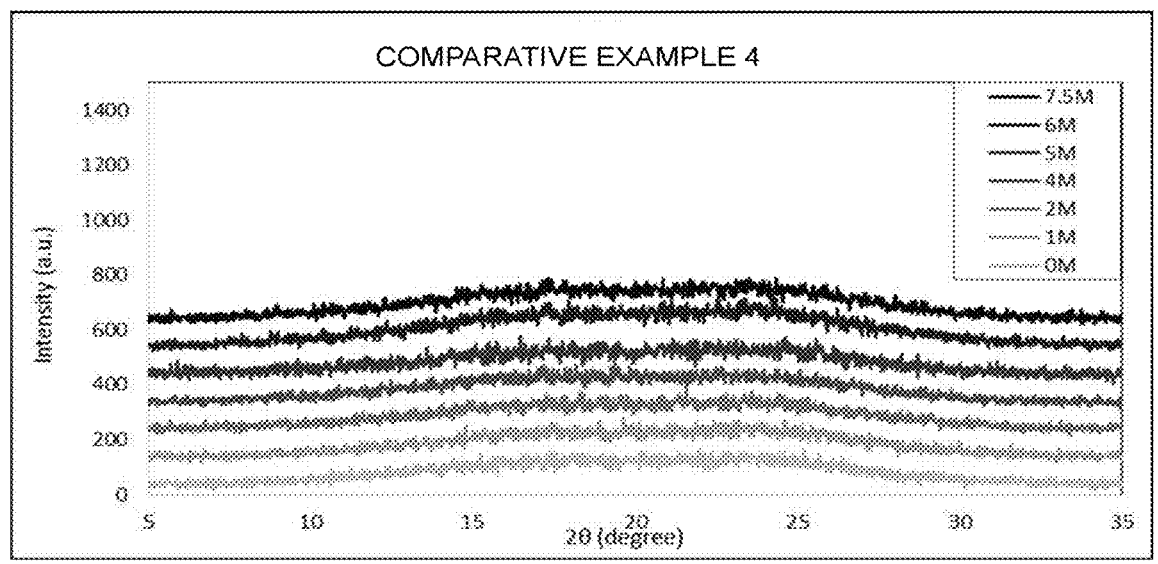
FIG. 14 illustrates storage stability (P-XRD) of a curcumin-containing composition (Comparative Example 4).
Figure 15:
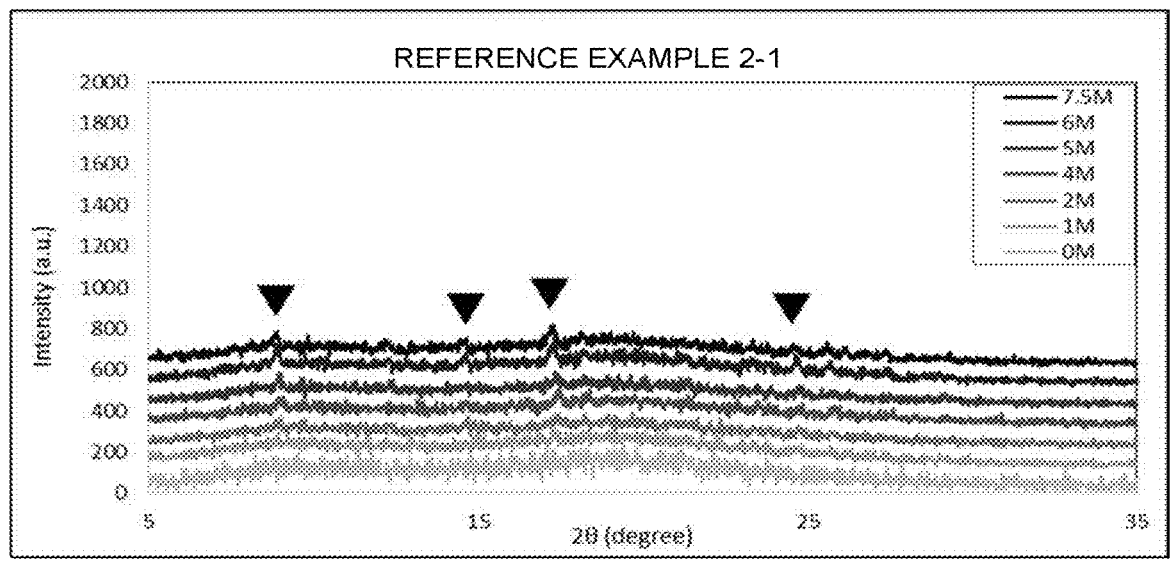
FIG. 15 illustrates storage stability (P-XRD) of a curcumin-containing composition (Reference Example 2-1).
Figure 16:
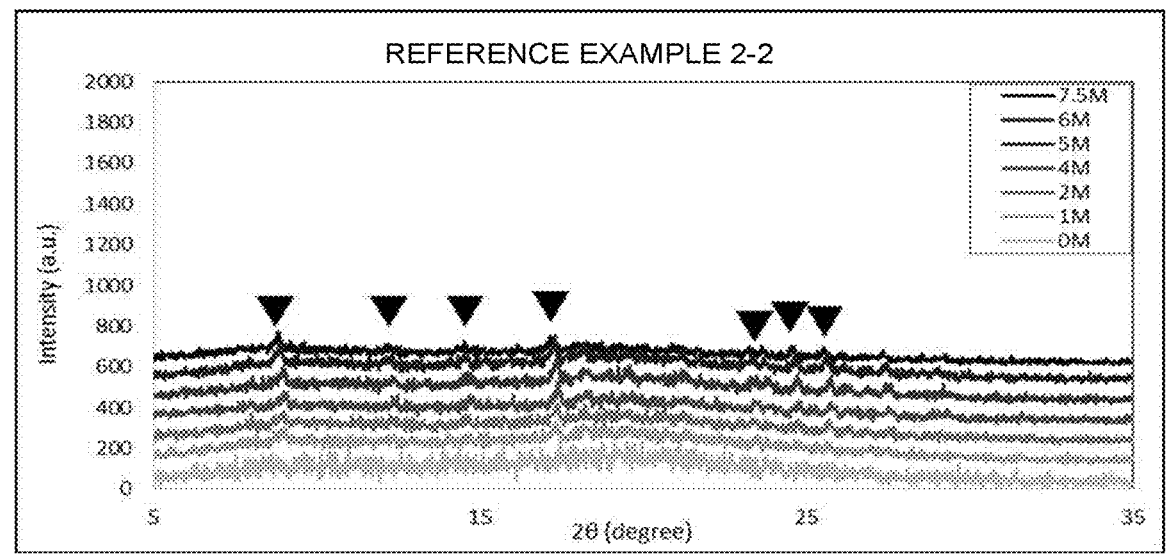
FIG. 16 illustrates storage stability (P-XRD) of a curcumin-containing composition (Reference Example 2-2).
Figure 17:
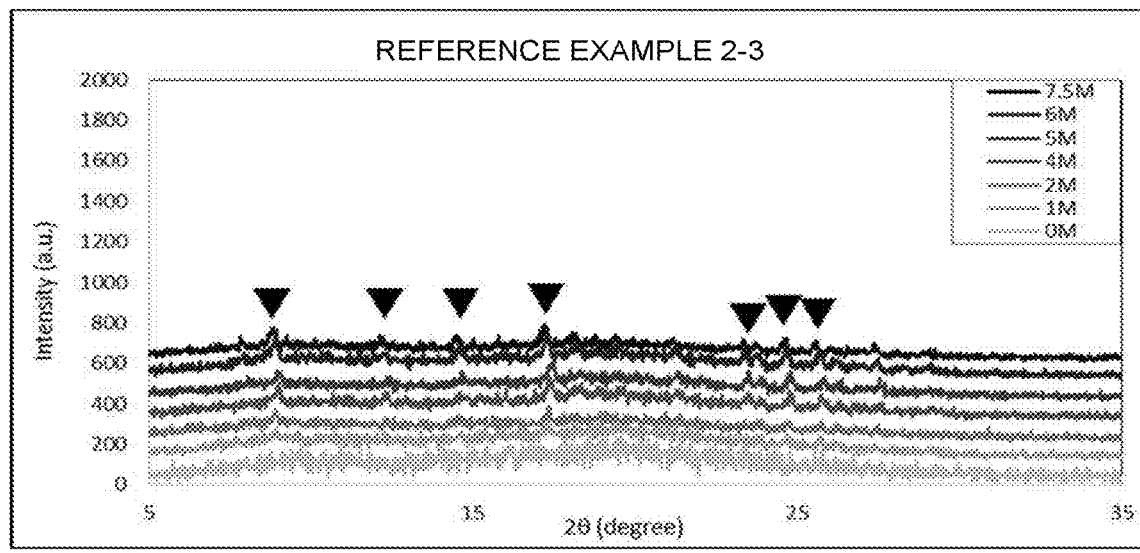
FIG. 17 illustrates storage stability (P-XRD) of a curcumin-containing composition (Reference Example 2-3).

As illustrated in FIGS. 8 to 11, in Examples 2 to 5, no peak indicating a crystal derived from curcumin was observed even 7.5 months after the start of the test. Similarly, as illustrated in FIG. 14, also in Comparative Example 4, no peak indicating a crystal derived from curcumin was observed from the start of the test to 7.5 months after the start of the test. Meanwhile, as illustrated in FIG. 12, in Comparative Example 1 containing only melted curcumin powder, a peak (arrow head) indicating a crystal derived from curcumin was observed four months after the start of the test. As illustrated in FIGS. 15 to 17, in Reference Examples 2-1 to 2-3 in which complexing was performed for 30 minutes, 60 minutes, and 120 minutes, respectively, a peak (arrow head) indicating a crystal derived from curcumin was observed one to two months after the start of the test. Note that the peak indicating a crystal derived from curcumin is determined from a peak in Comparative Example 2 (commercially available turmeric extract powder) in FIG. 13.

As described above, Examples 2 to 5 of the physically mixed formulation prepared by using melted curcumin powder, and in addition to the above, Comparative Example 4 which is a simple mixture obtained by adding 0.00175 parts by mass of trace HPMC to 1 part by mass of melted curcumin powder were found to suppress recrystallization of amorphous state curcumin and maintain the amorphous state favorably as compared with Comparative Example 1 containing only melted curcumin powder and Reference Examples 2-1 to 2-3 of the complex (solid dispersion).

Example 18: Absorbability Test after Oral Administration to rat in Examples 6 and 7

(1) Administration Method
To a 7 to 8 week-old male SD rat, a suspension obtained by suspending each of the amorphous curcumin-containing physically mixed formulations in Example 6 and 7 and Comparative Examples 5 to 8 in physiological saline was forcibly orally administered such that the curcumin concentration was 10 mg/kg. Blood was collected before administration, 30 minutes after administration, one hour after administration, and two hours after administration. The total curcumin concentration in plasma collected was measured by the method described in Example 15.

Figure 18:
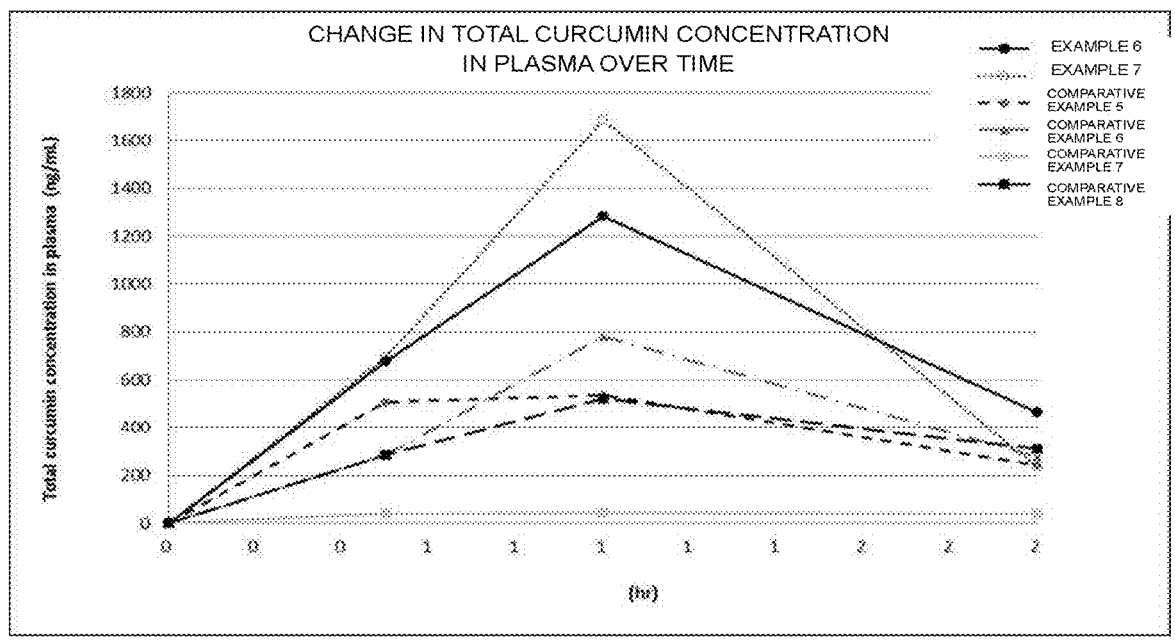
FIG. 18 illustrates absorbability (change over time) of curcumin-containing compositions (Examples 6 and 7 and Comparative Examples 5 to 8) after oral administration.
Figure 19:
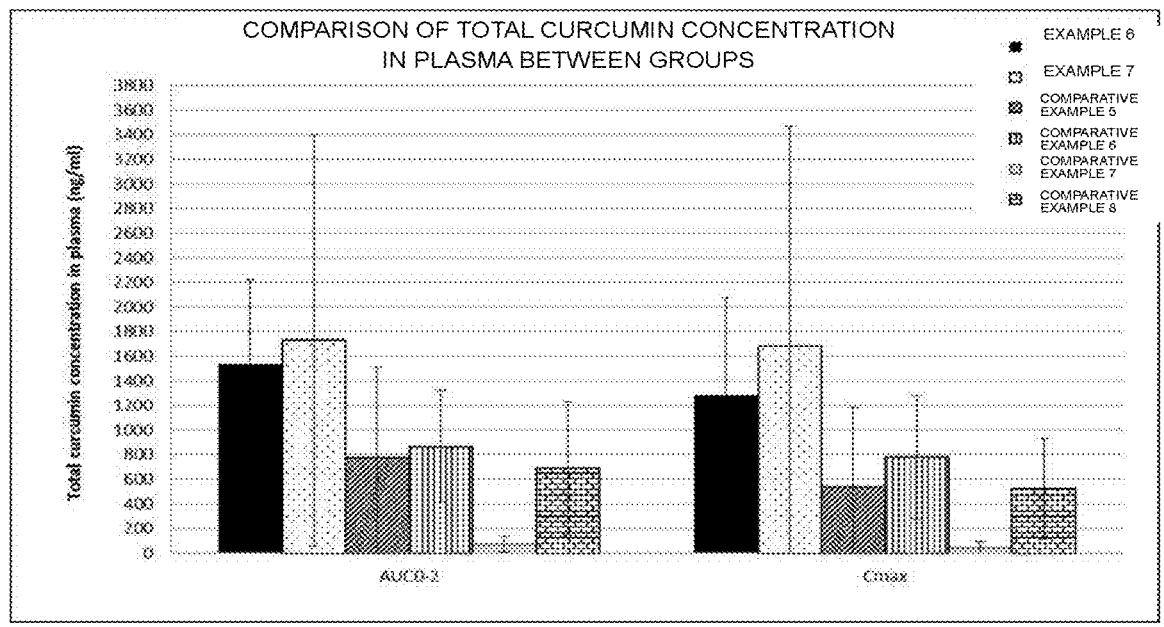
FIG. 19 illustrates absorbability (AUC and Cmax) of curcumin-containing compositions (Examples 6 and 7 and Comparative Examples 5 to 8) after oral administration.

(2) Result
A change in total curcumin concentration in plasma over time, a maximum blood concentration of total curcumin in plasma (Cmax (ng/mL)), and the area under total curcumin concentration in plasma-time curve (AUC (ng/mL·0-2 h)) are illustrated in FIGS. 18 and 19 and Table 6.

As illustrated in Table 6, the values of Cmax and AUC increased in order of Comparative Example 7, Comparative Example 8, Comparative Example 5, Comparative Example 6, Example 6, and Example 7.

As described above, a result was obtained in which the absorbability of curcumin was dramatically improved by mixing curcumin with a water-soluble polymer that becomes viscous in an aqueous medium having a pH of 5 or more.

TABLE 6

| Administration sample | Cmax (ng/mL) | AUC (ng/mL · 0-2 h) |
|---|---|---|
| Example 6 | 1281.9 ± 792.9 | 1530.8 ± 694.9 |
| Example 7 | 1684.0 ± 1787.2 | 1728.3 ± 1668.6 |
| Comparative Example 5 | 535.5 ± 650.0 | 774.9 ± 732.7 |
| Comparative Example 6 | 781.5 ± 499.6 | 866.6 ± 455.5 |
| Comparative Example 7 | 44.6 ± 44.7 | 72.1 ± 63.6 |
| Comparative Example 8 | 521.5 ± 406.4 | 687.1 ± 543.5 |

Example 19: Acceleration Test Results of Examples 6 and 7

In order to examine stability of amorphous curcumin in each of the physically mixed formulations prepared by the method of the present invention (Examples 6 and 7), each of the samples in Examples 6 and 7 and Comparative Examples 5 to 8 was put in a 6-well plate and held at 40° C. at a humidity of 75°. Crystallinity of curcumin was examined at the start of the test (0 M) and 1×1.25 months after the start of the test (1×1.25 M) in a similar manner to Example 17.

Figure 20:
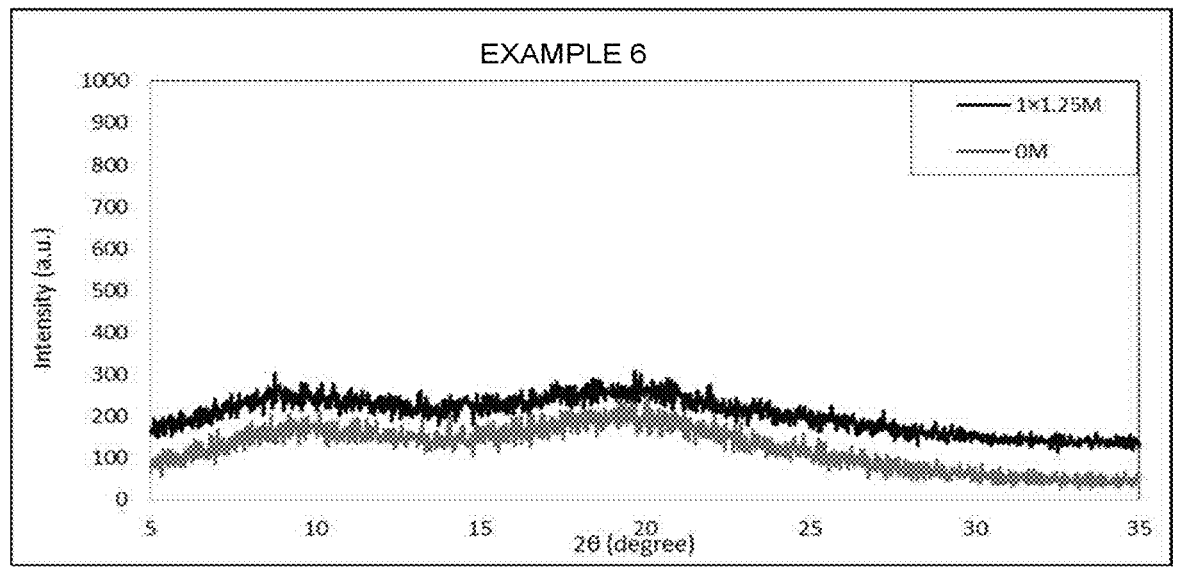
FIG. 20 illustrates storage stability (P-XRD) of a curcumin-containing composition (Example 6).
Figure 21:
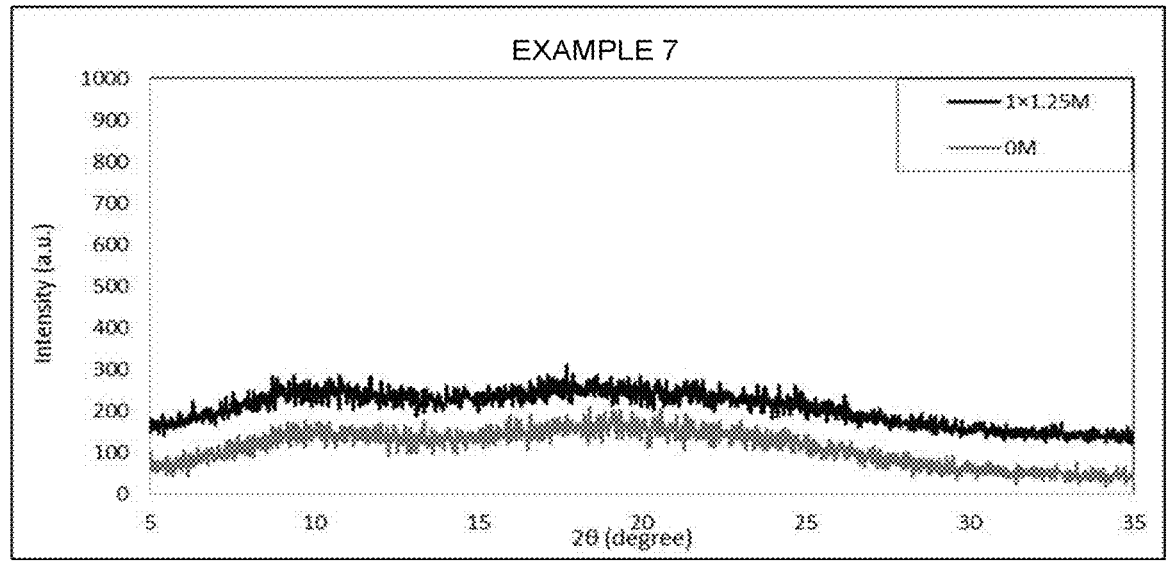
FIG. 21 illustrates storage stability (P-XRD) of a curcumin-containing composition (Example 7).
Figure 22:
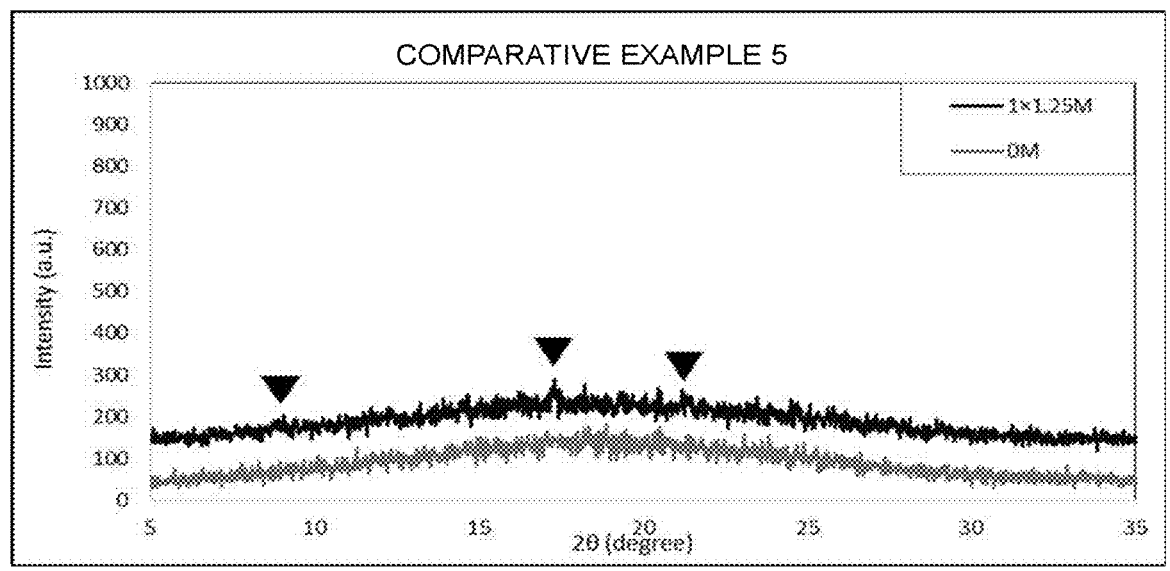
FIG. 22 illustrates storage stability (P-XRD) of a curcumin-containing composition (Comparative Example 5).
Figure 23:
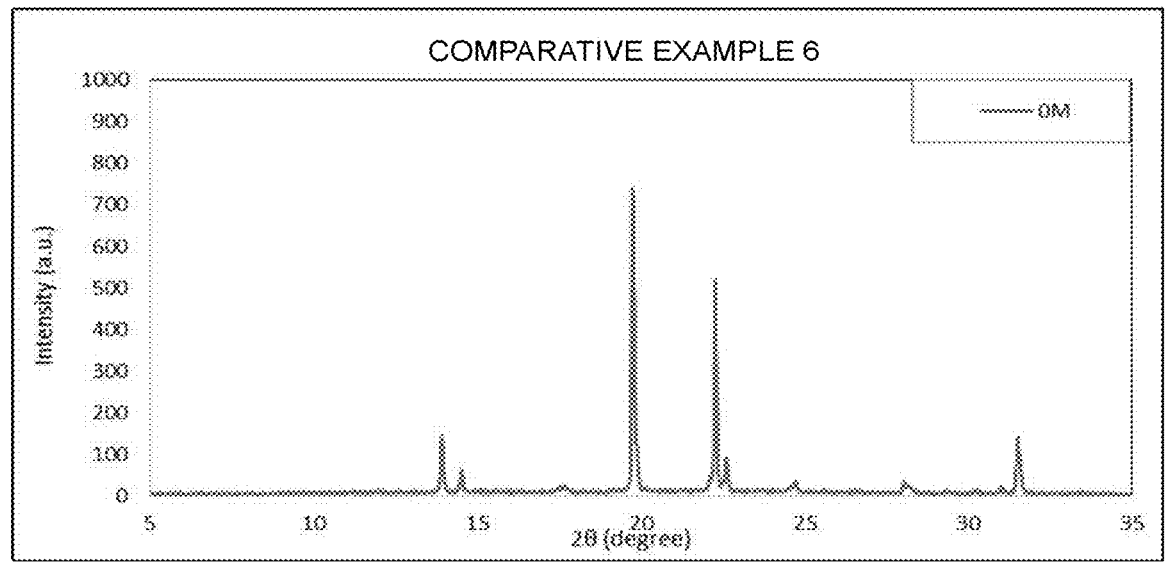
FIG. 23 illustrates storage stability (P-XRD) of a curcumin-containing composition (Comparative Example 6).
Figure 24:
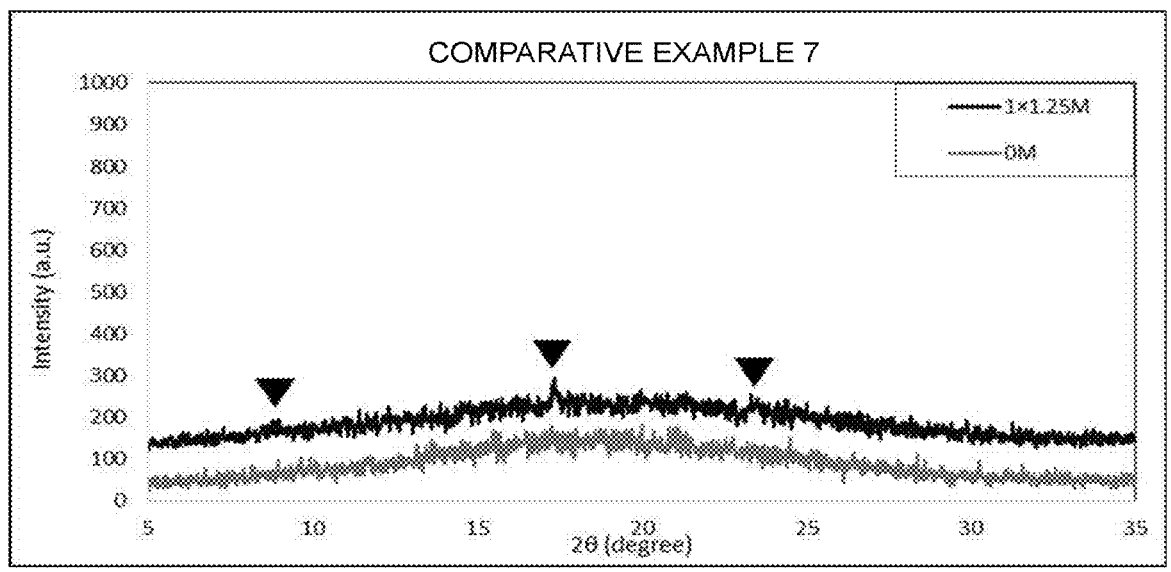
FIG. 24 illustrates storage stability (P-XRD) of a curcumin-containing composition (Comparative Example 7).
Figure 25:
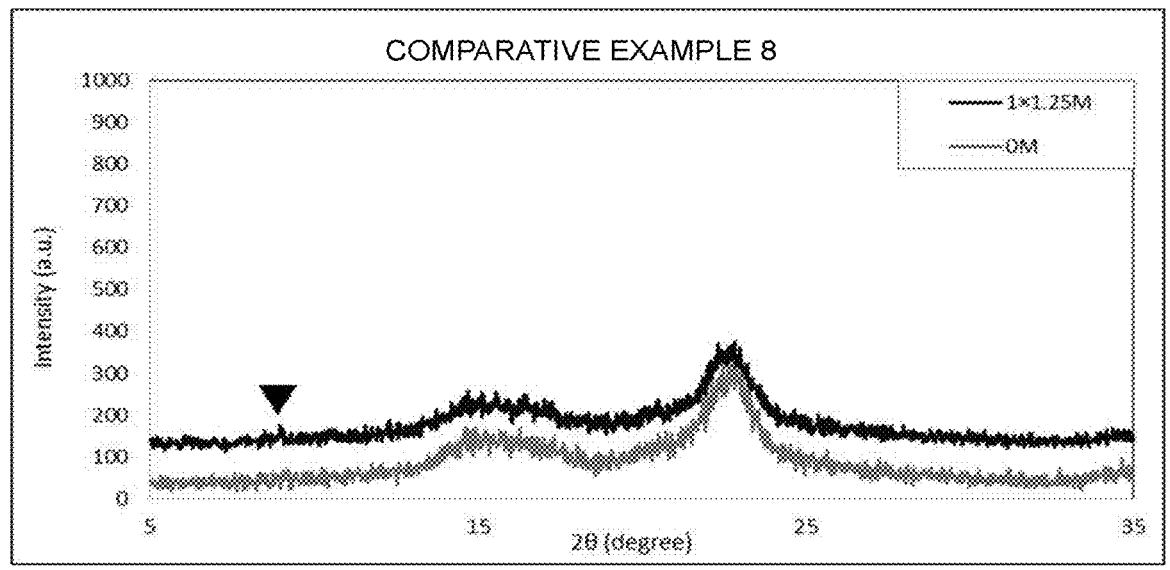
FIG. 25 illustrates storage stability (P-XRD) of a curcumin-containing composition (Comparative Example 8).

As illustrated in FIGS. 20 and 21, in Example 6 in which curcumin was mixed with HPMC and in Example 7 in which curcumin was mixed with HPMCAS, no peak indicating a crystal derived from curcumin was observed even 1×1.25 months after the start of the test. Meanwhile, as illustrated in FIGS. 22, 24, and 25, in Comparative Example 5 in which curcumin was mixed with modified starch, in Comparative Example 7 in which curcumin was mixed with maltodextrin, and in Comparative Example 8 in which curcumin was mixed with microcrystalline cellulose, a peak (arrow head) indicating a crystal derived from curcumin was observed 1 × 1.25 months after the start of the test. In Comparative Example 6 in which curcumin was mixed with xylitol in FIG. 23, moisture absorption and deliquesce occurred 1×1.25 months after the start of the test.

As described above, it was found that by mixing HPMC or HPMCAS with melted curcumin powder, recrystallization of amorphous state curcumin was suppressed and the amorphous state was maintained favorably.

Example 20: Acceleration Test Results of Example 8

In order to examine stability of amorphous curcumin in Example 8 prepared for industrial application of the present invention, the sample in Example 8 was put in an aluminum pouch and held at 40° C. Crystallinity of curcumin was examined at the start of the test (0 M) and 1 to 2×1.25 months after the start of the test (1, 1×1.25, 2, and 2×1.25 M) in a similar manner to Example 17.

Figure 26:
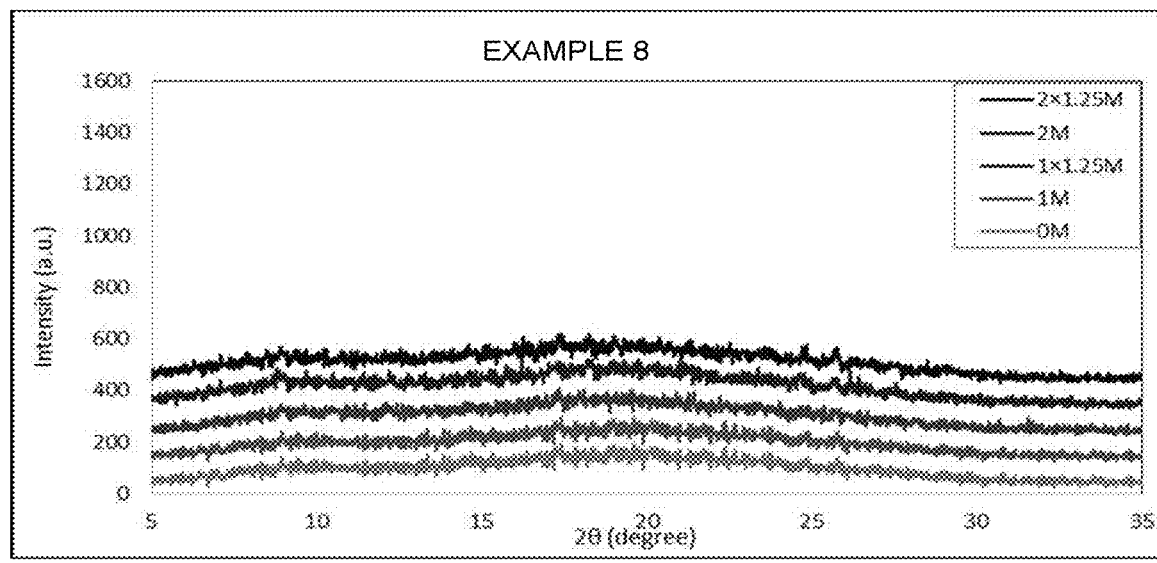
FIG. 26 illustrates storage stability (P-XRD) of a curcumin-containing composition (Example 8).

As illustrated in FIG. 26, in Example 8, no significant increase in the peak indicating a crystal derived from curcumin was observed from the start of the test to 2×1.25 months after the start of the test. In order to evaluate an increase in a curcumin crystal, the crystalline curcumin content was calculated from the integrated intensity under the crystal peak derived from curcumin in a range of a diffraction angle 2θ=8.2 to 9.3. As a result, as illustrated in Table 7, the content was about 10.4% 2×1.25 months after the start of the test.

TABLE 7

| Storage condition | Storage period | Integrated intensity | Crystal content (%) |
|---|---|---|---|
| Light-shielded, 40° C. | 0 months | 0.0 | 0.0 |
| | 1 × 1.25 months | 3.76 | 4.8 |
| | 2 × 1.25 months | 8.13 | 10.4 |

Example 21: Absorbability test of crystalline curcumin-containing formulation after oral administration to rat (1) Administration Method To a 7 to 8 week-old male SD rat, a suspension obtained by suspending a formulation prepared by using melted curcumin powder containing crystalline curcumin in each of Examples 9 to 12 (crystalline curcumin content 10 to 40%), HPMC (Metolose SE-50 manufactured by Shin-Etsu Chemical Co., Ltd.), and maltodextrin (NSD #300 manufactured by San-ei Sucrochemical Co., Ltd.) in physiological saline was forcibly orally administered such that the curcumin concentration was 10 mg/kg. Blood was collected before administration, 30 minutes after administration, one hour after administration, and two hours after administration. The total curcumin concentration in plasma collected was measured by the method described in Example 15.

(2) Result

A change in total curcumin concentration in plasma over time, a maximum blood concentration of total curcumin in plasma (Cmax (ng/mL)), and the area under total curcumin concentration in plasma-time curve (AUC (ng/mL·0-2 h)) increased in order of a sample in which the content of crystalline curcumin was 40%, a sample in which the content of crystalline curcumin was 30%, a sample in which the content of crystalline curcumin was 20°, and a sample in which the content of crystalline curcumin was 10%.

Example 22: Absorbability Test of Composition Containing Amorphous Body of other Compound after Oral Administration to Rat Examples 15, 16, 18, and 21 indicate that the composition of the present invention containing an amorphous body of curcumin, which is a polyphenol, and a hydrophilic polymer has excellent oral absorbability. In order to examine whether a similar effect could be expected with a compound other than a polyphenol, a composition similar to the composition of the present invention was prepared using nifedipine. The composition was administered to a rat, and a blood concentration was measured.

(1) Administration Method

To a 8 to 9 week-old male SD rat, a suspension obtained by suspending each of the amorphous nifedipine-containing physically mixed formulations in Comparative Examples 9 to 14 in physiological saline was forcibly orally administered such that the nifedipine concentration was 1 mg/kg. Blood was collected before administration, one hour after administration, two hours after administration, four hours after administration, and six hours after administration, and the nifedipine concentration in plasma collected was measured by the method described below.

(2) Measurement of Nifedipine Concentration in Plasma

The nifedipine concentration in plasma was measured according to the method of A. Nishimura et al. (J. Health Science, 56 (3), 310-320, 2010).

Result: Change in nifedipine concentration in plasma in Comparative Examples and comparison Table 8 illustrates a change in a nifedipine concentration in plasma in Comparative Examples.

TABLE 8

| | Before administration | One hour after administration | Two hours after administration | Four hours after administration | Six hours after administration |
|---|---|---|---|---|---|
| Comparative Example 9 | 0 | 38 | 41 | 28 | 19 |
| Comparative Example 10 | 0 | 28 | 40 | 43 | 33 |
| Comparative Example 11 | 0 | 67 | 30 | 16 | 20 |
| Comparative Example 12 | 0 | 58 | 72 | 30 | 27 |
| Comparative Example 13 | 0 | 69 | 55 | 47 | 28 |
| Comparative Example 14 | 0 | 40 | 60 | 35 | 20 |

(unit: ng/mL)

As can be seen from Table 8, in the case of amorphous nifedipine, such a difference in absorbability depending on the type of mixed polymer or the like as observed in the case of amorphous curcumin was not observed, and no significant oral absorption promoting effect was observed in HPMC or HPMCAS. Therefore, it can be said that the oral absorption promoting effect exhibited by the mixture of amorphous curcumin and HPMC or HPMCAS of the present application is extremely specific.

The invention claimed is:

1. An oral ingestion composition, comprising:
   (A) solid curcumin or a turmeric pigment, comprising an amorphous body (A-2) and optionally a crystalline body (A-1), such that a content mass ratio (A-1/A-2) of the crystalline body (A-1) to the amorphous body (A-2) is 0.67 or less; and
   (B) at least one solid water-soluble polymer which becomes viscous in an aqueous medium having a pH of 5 or more,
   wherein the component (B) is at least one selected from the group consisting of hydroxypropyl cellulose, hydroxypropyl methyl cellulose, carboxymethyl cellulose, carboxymethyl cellulose sodium, methyl cellulose, hydroxypropyl methyl cellulose acetate succinate, carboxymethyl ethyl cellulose, and hydroxypropyl methyl cellulose phthalate ester,
   wherein the composition comprises the component (A) and the component (B) in a uniformly mixed state, and wherein the composition is obtainable by mixing the component (A) and the component (B) in their solid state.

2. The composition of claim 1, wherein a content mass ratio (A/B) of the components (A) and (B) is in a range of from 0.1 to 570.

3. The composition of claim 1, wherein the component (A) is solid curcumin.

4. The composition of claim 1, wherein the component (A) and the component (B) each have a particle size of 300 μm or less.

5. A method for manufacturing the composition of claim 1, the method comprising:
  melting and then cooling curcumin or a turmeric pigment, thereby producing the amorphous body (A-2); and
  pulverizing and mixing individually or simultaneously the amorphous body (A-2) and the component (B).

6. The method of claim 5, wherein the pulverizing and mixing comprises rotary type pulverizing, air flow pulverizing, high speed rotary pulverizing, container driving pulverizing, or medium stirring pulverizing.

7. A feed, a food, a drink, or a drug, comprising the composition of claim 1.

8. The composition of claim 1, wherein the component (A) is a turmeric pigment.

9. The composition of claim 1, wherein the component (A) comprises the amorphous body (A-2) and the crystalline body (A-1).

10. The composition of claim 1, wherein the component (B) comprises hydroxypropyl cellulose.

11. The composition of claim 1, wherein the component (B) comprises hydroxypropyl ethyl cellulose.

12. The composition of claim 1, wherein the component (B) comprises carboxymethyl cellulose.

13. The composition of claim 1, wherein the component (B) comprises methyl cellulose.

14. The composition of claim 1, wherein a content mass ratio (A/B) of the components (A) and (B) is in a range of from 0.5 to 50.

15. The composition of claim 1, wherein the component (A) and the component (B) are not forming a complex in the composition.

* * * * *